(12) United States Patent
Cowan et al.

(10) Patent No.: US 11,839,751 B2
(45) Date of Patent: Dec. 12, 2023

(54) IN-LINE AIR BUBBLE SUSPENSION APPARATUS FOR ANGIOGRAPHY INJECTOR FLUID PATHS

(71) Applicant: BAYER HEALTHCARE LLC, Whippany, NJ (US)

(72) Inventors: Kevin Cowan, Allison Park, PA (US); James Dedig, Pittsburgh, PA (US); Michael Spohn, Fenelton, PA (US); John Haury, Sewickley, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 17/999,092

(22) PCT Filed: Jun. 16, 2021

(86) PCT No.: PCT/US2021/037623
§ 371 (c)(1),
(2) Date: Nov. 17, 2022

(87) PCT Pub. No.: WO2021/257699
PCT Pub. Date: Dec. 23, 2021

(65) Prior Publication Data
US 2023/0191041 A1 Jun. 22, 2023

Related U.S. Application Data

(60) Provisional application No. 62/705,250, filed on Jun. 18, 2020.

(51) Int. Cl.
*A61M 5/36* (2006.01)
*A61M 5/00* (2006.01)
*A61M 5/145* (2006.01)

(52) U.S. Cl.
CPC ............ *A61M 5/365* (2013.01); *A61M 5/007* (2013.01); *A61M 5/14546* (2013.01)

(58) Field of Classification Search
CPC ........ A61M 2039/226; A61M 2206/16; A61M 39/22; A61M 5/16809; A61M 5/36;
(Continued)

(56) References Cited

U.S. PATENT DOCUMENTS

| 352,715 A | 11/1886 | Sandmark |
|---|---|---|
| 508,584 A | 11/1893 | Stevens |

(Continued)

FOREIGN PATENT DOCUMENTS

| CN | 103917269 A | 7/2014 |
|---|---|---|
| CN | 105521533 A | 4/2016 |

(Continued)

OTHER PUBLICATIONS

"International Preliminary Report on Patentability from PCT Application No. PCT/US2021/037623", dated Dec. 29, 2022.

(Continued)

*Primary Examiner* — Brandy S Lee
(74) *Attorney, Agent, or Firm* — Joseph L. Kent; James R. Stevenson; David Schramm

(57) ABSTRACT

An apparatus (300) for suspending air bubbles in a fluid path of a fluid injector system includes an internal chamber (320) having a curved interior wall (322) defined within the housing (310), an inlet fluid pathway in fluid communication with the internal chamber, and an outlet fluid pathway in fluid communication with the internal chamber. The inlet fluid pathway extending into the chamber at a tangent to the curved interior wall, and the outlet fluid pathway spaced from the inlet fluid pathway such that fluid flowing into the internal chamber via the inlet fluid pathway is directed away from the outlet fluid pathway. The internal chamber is (Continued)

configured to create an internal fluid vortex in an injection fluid entering the internal chamber from the inlet fluid pathway, and wherein the internal fluid vortex at least temporarily suspends air bubbles in the fluid in the internal vortex and delays the passage of the air bubbles to the outlet fluid pathway.

21 Claims, 22 Drawing Sheets

(58) Field of Classification Search
CPC .................. A61M 5/365; A61M 5/385; A61M 2005/3123; A61M 5/007; A61M 5/142; A61M 5/14546; A61M 5/16827; A61M 5/16831
See application file for complete search history.

(56) References Cited

U.S. PATENT DOCUMENTS

| | | | |
|---|---|---|---|
| 798,093 A | 8/1905 | Edward |
| 817,054 A | 4/1906 | Daniel |
| 937,029 A | 10/1909 | Blessing et al. |
| 945,143 A | 1/1910 | Iacques |
| 1,388,946 A | 8/1921 | Goold |
| 1,930,929 A | 10/1933 | Joel et al. |
| 2,062,285 A | 12/1936 | Sam et al. |
| 2,511,291 A | 6/1950 | Mueller |
| 2,514,575 A | 7/1950 | Hein et al. |
| 2,583,206 A | 1/1952 | Borck et al. |
| 2,592,381 A | 4/1952 | Blackman |
| 2,616,422 A | 11/1952 | Jones |
| 2,667,163 A | 1/1954 | Smith |
| 2,667,164 A | 1/1954 | Smith |
| 2,667,165 A | 1/1954 | Smith |
| 2,667,872 A | 2/1954 | Smith |
| 2,672,866 A | 3/1954 | Kater |
| 2,673,561 A | 3/1954 | Peterson, Jr. |
| 2,688,963 A | 9/1954 | Smith |
| 2,688,964 A | 9/1954 | Smith |
| 2,690,179 A | 9/1954 | Fox |
| 2,717,598 A | 9/1955 | Krasno |
| 2,805,662 A | 9/1957 | Lawshe et al. |
| 2,911,972 A | 11/1959 | Elinger |
| 2,915,986 A | 12/1959 | Sisson |
| 2,935,067 A | 5/1960 | Bouet |
| 2,950,717 A | 8/1960 | Bonet |
| 3,101,712 A | 8/1963 | Strazdins et al. |
| 3,155,281 A | 11/1964 | Stracey |
| 3,159,312 A | 12/1964 | Van Sciver, II |
| 3,161,194 A | 12/1964 | Chapman |
| 3,161,195 A | 12/1964 | Taylor et al. |
| 3,166,070 A | 1/1965 | Everett |
| 3,172,577 A | 3/1965 | Hartung |
| 3,190,619 A | 6/1965 | Penney et al. |
| 3,199,511 A | 8/1965 | Kulick |
| 3,231,139 A | 1/1966 | Bouet |
| 3,276,472 A | 10/1966 | Jinkens et al. |
| 3,301,293 A | 1/1967 | Santelli |
| 3,340,869 A | 9/1967 | Bane |
| 3,353,537 A | 11/1967 | Knox et al. |
| 3,390,821 A | 7/1968 | Mullan |
| 3,411,503 A | 11/1968 | Santomieri |
| 3,412,906 A | 11/1968 | Dinger |
| 3,442,424 A | 5/1969 | Sam et al. |
| 3,471,058 A | 10/1969 | Peter et al. |
| 3,473,524 A | 10/1969 | John |
| 3,474,844 A | 10/1969 | Rudolph et al. |
| 3,506,163 A | 4/1970 | James et al. |
| 3,507,278 A | 4/1970 | Winfried |
| 3,527,215 A | 9/1970 | Harry |
| 3,557,788 A | 1/1971 | Swartz |
| 3,613,963 A | 10/1971 | Berkmuller |
| 3,618,846 A | 11/1971 | Poli |
| 3,631,654 A * | 1/1972 | Riely ................. B01D 46/10 |
| | | | 96/6 |
| 3,635,444 A | 1/1972 | Potter |
| 3,671,208 A | 6/1972 | Medsker |
| 3,699,961 A | 10/1972 | Szpur |
| 3,719,207 A | 3/1973 | Takeda |
| 3,736,932 A | 6/1973 | Satchell |
| 3,785,367 A | 1/1974 | Fortin et al. |
| 3,826,409 A | 7/1974 | Chilcoate |
| 3,868,967 A | 3/1975 | Harding |
| 3,873,003 A | 3/1975 | Seiferth et al. |
| 3,938,514 A | 2/1976 | Boucher |
| 3,998,223 A | 12/1976 | Dawe |
| 4,035,461 A | 7/1977 | Korth |
| 4,041,944 A | 8/1977 | Rhodes |
| 4,044,836 A | 8/1977 | Martin et al. |
| 4,064,879 A | 12/1977 | Leibinsohn |
| 4,066,080 A | 1/1978 | Sneider |
| 4,131,217 A | 12/1978 | Sandegren |
| 4,136,802 A | 1/1979 | Mascia et al. |
| 4,140,117 A | 2/1979 | Buckles et al. |
| 4,171,698 A | 10/1979 | Genese |
| 4,204,775 A | 5/1980 | Speer |
| 4,208,136 A | 6/1980 | King et al. |
| 4,236,516 A | 12/1980 | Nilson |
| 4,245,655 A | 1/1981 | Patel |
| 4,312,344 A | 1/1982 | Nilson |
| 4,318,400 A | 3/1982 | Peery et al. |
| 4,325,369 A | 4/1982 | Nilson |
| 4,329,067 A | 5/1982 | Goudy, Jr. |
| 4,349,129 A | 9/1982 | Amneus |
| 4,392,491 A | 7/1983 | Takasugi et al. |
| 4,411,656 A | 10/1983 | Cornett, III |
| 4,419,096 A | 12/1983 | Leeper et al. |
| 4,438,845 A | 3/1984 | Mochow |
| 4,441,823 A | 4/1984 | Power et al. |
| 4,444,310 A | 4/1984 | Odell |
| 4,526,296 A | 7/1985 | Berger et al. |
| 4,610,665 A | 9/1986 | Matsumoto et al. |
| 4,741,733 A | 5/1988 | Winchell et al. |
| 4,747,839 A | 5/1988 | Tarello et al. |
| 4,753,638 A | 6/1988 | Peters |
| 4,773,458 A | 9/1988 | Touzani |
| 4,824,145 A | 4/1989 | Carlsson |
| 4,850,807 A | 7/1989 | Frantz |
| 4,895,570 A | 1/1990 | Larkin |
| 4,904,239 A | 2/1990 | Winchell et al. |
| 4,952,068 A | 8/1990 | Flint |
| 5,000,739 A | 3/1991 | Kulisz et al. |
| 5,011,477 A | 4/1991 | Winchell et al. |
| 5,026,348 A | 6/1991 | Venegas |
| 5,033,631 A | 7/1991 | Nightingale |
| 5,048,684 A | 9/1991 | Scott |
| 5,120,315 A | 6/1992 | Hessel |
| 5,147,311 A | 9/1992 | Pickhard |
| 5,163,928 A | 11/1992 | Hobbs et al. |
| 5,178,610 A | 1/1993 | Tsujikawa et al. |
| 5,192,272 A | 3/1993 | Faure |
| 5,199,567 A | 4/1993 | Discko, Jr. |
| 5,201,438 A | 4/1993 | Norwood |
| 5,209,372 A | 5/1993 | Norwood |
| 5,236,204 A | 8/1993 | Hempel |
| 5,237,309 A | 8/1993 | Frantz et al. |
| 5,238,003 A | 8/1993 | Baidwan et al. |
| 5,238,150 A | 8/1993 | Williams |
| 5,240,130 A | 8/1993 | Osbakk |
| 5,242,422 A | 9/1993 | Schneberger et al. |
| 5,263,940 A | 11/1993 | Kriesel |
| 5,269,428 A | 12/1993 | Gilbert |
| 5,312,018 A | 5/1994 | Evezich |
| 5,316,452 A | 5/1994 | Bogen et al. |
| 5,318,520 A | 6/1994 | Nakao |
| 5,318,540 A | 6/1994 | Athayde et al. |
| 5,333,761 A | 8/1994 | Davis et al. |
| 5,342,313 A | 8/1994 | Campbell et al. |
| 5,353,961 A | 10/1994 | Debush |
| 5,370,250 A | 12/1994 | Gilbert |
| 5,383,858 A | 1/1995 | Reilly et al. |
| 5,397,157 A | 3/1995 | Hempel et al. |

(56) References Cited

U.S. PATENT DOCUMENTS

| | | |
|---|---|---|
| 5,399,173 A | 3/1995 | Parks et al. |
| 5,431,185 A | 7/1995 | Shannon et al. |
| 5,492,147 A | 2/1996 | Challender et al. |
| 5,520,653 A | 5/1996 | Reilly et al. |
| 5,573,129 A | 11/1996 | Nagata et al. |
| 5,578,005 A | 11/1996 | Sancoff et al. |
| 5,584,413 A | 12/1996 | Jung |
| 5,592,948 A | 1/1997 | Gatten |
| 5,609,580 A | 3/1997 | Kwiatkowski et al. |
| 5,615,791 A | 4/1997 | Vatelot et al. |
| 5,638,995 A | 6/1997 | Mazda |
| 5,651,776 A | 7/1997 | Appling et al. |
| 5,683,369 A | 11/1997 | Tsukada |
| 5,725,500 A | 3/1998 | Micheler |
| 5,758,789 A | 6/1998 | Shin et al. |
| 5,794,107 A | 8/1998 | Russell |
| 5,827,233 A | 10/1998 | Futagawa et al. |
| 5,836,922 A | 11/1998 | Hansen et al. |
| 5,873,861 A | 2/1999 | Hitchins et al. |
| 5,893,843 A | 4/1999 | Rodrigues Claro |
| 5,899,889 A | 5/1999 | Futagawa et al. |
| 5,935,105 A | 8/1999 | Manning et al. |
| 5,957,898 A | 9/1999 | Jepson et al. |
| RE36,377 E | 11/1999 | Gilbert |
| 5,976,112 A | 11/1999 | Lyza, Jr. |
| 5,979,326 A | 11/1999 | Ohinata |
| 5,980,489 A | 11/1999 | Kriesel |
| 6,054,194 A | 4/2000 | Kane |
| 6,056,724 A | 5/2000 | Acroix |
| 6,062,437 A | 5/2000 | Mascitelli |
| 6,063,058 A | 5/2000 | Sakamoto |
| 6,077,252 A | 6/2000 | Siegel |
| 6,105,815 A | 8/2000 | Mazda |
| 6,132,396 A | 10/2000 | Antanavich et al. |
| 6,142,976 A | 11/2000 | Kubo |
| 6,159,183 A | 12/2000 | Neer et al. |
| 6,177,049 B1 | 1/2001 | Schnell et al. |
| 6,216,915 B1 | 4/2001 | Harman et al. |
| 6,224,577 B1 | 5/2001 | Dedola et al. |
| 6,250,505 B1 | 6/2001 | Petit |
| 6,270,482 B1 | 8/2001 | Rosoff et al. |
| 6,306,191 B1 | 10/2001 | McInerney et al. |
| 6,315,761 B1 | 11/2001 | Shcherbina et al. |
| 6,319,235 B1 | 11/2001 | Yoshino |
| 6,322,535 B1 | 11/2001 | Hitchins et al. |
| 6,322,542 B1 | 11/2001 | Nilson et al. |
| 6,328,715 B1 | 12/2001 | Dragan et al. |
| 6,332,876 B1 | 12/2001 | Poynter et al. |
| 6,442,418 B1 | 8/2002 | Evans, III et al. |
| 6,450,993 B1 | 9/2002 | Lin |
| 6,465,024 B1 | 10/2002 | Di et al. |
| 6,485,471 B1 | 11/2002 | Zivitz et al. |
| 6,497,684 B2 | 12/2002 | Witowski et al. |
| 6,558,358 B2 | 5/2003 | Rosoff et al. |
| 6,575,930 B1 | 6/2003 | Trombley, III et al. |
| 6,578,738 B1 | 6/2003 | Keller |
| 6,616,000 B1 | 9/2003 | Renz |
| 6,620,134 B1 | 9/2003 | Trombley, III et al. |
| 6,634,524 B1 | 10/2003 | Helmenstein |
| 6,643,537 B1 | 11/2003 | Zatezalo et al. |
| 6,652,489 B2 | 11/2003 | Trocki et al. |
| 6,702,143 B2 | 3/2004 | Wang |
| 6,716,195 B2 | 4/2004 | Nolan, Jr. et al. |
| 6,723,074 B1 | 4/2004 | Halseth |
| 6,726,657 B1 | 4/2004 | Dedig et al. |
| 6,731,971 B2 | 5/2004 | Evans et al. |
| 6,773,417 B2 | 8/2004 | Fitzgibbons et al. |
| 6,827,862 B1 * | 12/2004 | Brockhoff .................. B04C 3/00 96/155 |
| 6,840,164 B2 | 1/2005 | Eastman |
| 6,855,130 B2 | 2/2005 | Saulenas et al. |
| 6,866,039 B1 | 3/2005 | Wright et al. |
| 6,866,654 B2 | 3/2005 | Callan et al. |
| 6,869,419 B2 | 3/2005 | Dragan et al. |
| 6,921,384 B2 | 7/2005 | Reilly et al. |
| RE38,770 E | 8/2005 | Gilbert |
| 6,974,443 B2 | 12/2005 | Reilly et al. |
| 6,984,222 B1 | 1/2006 | Hitchins et al. |
| 7,004,213 B2 | 2/2006 | Jansen |
| 7,011,650 B2 | 3/2006 | Rosoff et al. |
| 7,094,216 B2 | 8/2006 | Trombley, III et al. |
| 7,101,352 B2 | 9/2006 | Dochon et al. |
| 7,192,416 B1 | 3/2007 | Lazzaro et al. |
| 7,192,549 B2 | 3/2007 | Hansen |
| 7,240,926 B2 | 7/2007 | Dalle et al. |
| 7,250,039 B2 | 7/2007 | Fitzgerald |
| 7,309,463 B2 | 12/2007 | Hansen |
| 7,351,221 B2 | 4/2008 | Trombley, III et al. |
| 7,419,478 B1 | 9/2008 | Reilly et al. |
| 7,427,281 B2 | 9/2008 | Uber et al. |
| 7,457,804 B2 | 11/2008 | Uber, III et al. |
| 7,462,166 B2 | 12/2008 | Kowan et al. |
| 7,497,843 B1 | 3/2009 | Castillo et al. |
| 7,513,378 B2 | 4/2009 | Mori et al. |
| 7,540,856 B2 | 6/2009 | Hitchins et al. |
| 7,553,294 B2 | 6/2009 | Lazzaro et al. |
| 7,556,619 B2 | 7/2009 | Spohn et al. |
| 7,563,249 B2 | 7/2009 | Schriver et al. |
| 7,581,559 B2 | 9/2009 | Bausmith et al. |
| 7,597,683 B2 | 10/2009 | Myhrberg et al. |
| 7,604,623 B2 | 10/2009 | Brunner et al. |
| 7,611,503 B2 | 11/2009 | Spohn et al. |
| 7,621,395 B2 | 11/2009 | Mogensen et al. |
| 7,666,169 B2 | 2/2010 | Cowan et al. |
| 7,686,788 B2 | 3/2010 | Freyman et al. |
| 7,766,883 B2 | 8/2010 | Reilly et al. |
| 7,802,691 B2 | 9/2010 | Musalek et al. |
| 7,818,992 B2 | 10/2010 | Riley et al. |
| 7,861,893 B2 | 1/2011 | Voegele et al. |
| 7,996,381 B2 | 8/2011 | Uber, III et al. |
| 8,057,406 B2 | 11/2011 | Mohiuddin |
| 8,147,464 B2 | 4/2012 | Spohn et al. |
| 8,162,903 B2 | 4/2012 | Reilly et al. |
| 8,337,456 B2 | 12/2012 | Schriver et al. |
| 8,388,580 B2 | 3/2013 | Schriver et al. |
| 8,419,676 B2 | 4/2013 | Evans et al. |
| 8,439,863 B2 | 5/2013 | Fago et al. |
| 8,521,716 B2 | 8/2013 | Uber, III et al. |
| 8,540,698 B2 | 9/2013 | Spohn et al. |
| 8,740,877 B2 | 6/2014 | Borlaug et al. |
| 8,795,240 B2 | 8/2014 | Chelak |
| 8,872,708 B2 | 10/2014 | Hill et al. |
| 8,882,702 B2 | 11/2014 | Suchecki et al. |
| 8,882,708 B2 | 11/2014 | Hieb et al. |
| 8,919,384 B2 | 12/2014 | Spohn et al. |
| 8,945,051 B2 | 2/2015 | Schriver et al. |
| 8,992,489 B2 | 3/2015 | Spohn et al. |
| 9,173,995 B1 | 11/2015 | Tucker et al. |
| 9,180,252 B2 | 11/2015 | Gelblum et al. |
| 9,180,260 B2 | 11/2015 | Huang et al. |
| 9,199,033 B1 | 12/2015 | Cowan et al. |
| 9,474,857 B2 | 10/2016 | Riley et al. |
| 9,498,570 B2 | 11/2016 | Cowan et al. |
| 9,555,379 B2 | 1/2017 | Schriver et al. |
| 9,566,381 B2 | 2/2017 | Barron et al. |
| 9,649,436 B2 | 5/2017 | Capone et al. |
| 9,901,671 B2 | 2/2018 | Toews et al. |
| 10,022,493 B2 | 7/2018 | Shearer, Jr. et al. |
| 10,046,106 B2 | 8/2018 | Cowan et al. |
| 10,105,491 B2 | 10/2018 | Gelblum et al. |
| 10,124,110 B2 | 11/2018 | Dedig et al. |
| 10,188,849 B2 | 1/2019 | Fangrow |
| 10,201,666 B2 | 2/2019 | Cowan et al. |
| 10,398,353 B2 | 9/2019 | Addison et al. |
| 10,420,902 B2 | 9/2019 | Cowan et al. |
| 10,507,319 B2 | 12/2019 | Haury et al. |
| 10,549,084 B2 | 2/2020 | Sokolov et al. |
| 10,857,345 B2 | 12/2020 | Uber, III et al. |
| 11,083,882 B2 | 8/2021 | Schrauder et al. |
| 11,207,462 B2 | 12/2021 | Cowan et al. |
| 11,389,585 B2 | 7/2022 | Spohn et al. |
| 11,413,403 B2 | 8/2022 | Yoshioka et al. |
| 11,547,793 B2 | 1/2023 | Cowan et al. |
| 2001/0004466 A1 | 6/2001 | Heinz et al. |

(56) References Cited

U.S. PATENT DOCUMENTS

| | | |
|---|---|---|
| 2001/0018575 A1 | 8/2001 | Lyza |
| 2002/0147429 A1 | 10/2002 | Cowan et al. |
| 2003/0163084 A1* | 8/2003 | Griffiths ............ B01F 35/32021 604/82 |
| 2003/0216695 A1 | 11/2003 | Yang |
| 2003/0226539 A1 | 12/2003 | Kim et al. |
| 2004/0068224 A1 | 4/2004 | Couvillon et al. |
| 2004/0092905 A1 | 5/2004 | Azzolini |
| 2004/0116893 A1 | 6/2004 | Spohn et al. |
| 2004/0154788 A1 | 8/2004 | Symonds |
| 2004/0186457 A1 | 9/2004 | Truitt et al. |
| 2004/0249344 A1 | 12/2004 | Nemoto et al. |
| 2004/0254541 A1 | 12/2004 | Wong et al. |
| 2005/0082828 A1 | 4/2005 | Wicks et al. |
| 2005/0225082 A1 | 10/2005 | Dalle et al. |
| 2006/0052794 A1 | 3/2006 | McGill et al. |
| 2006/0149213 A1 | 7/2006 | Raybuck |
| 2006/0200083 A1 | 9/2006 | Freyman et al. |
| 2007/0068964 A1 | 3/2007 | Tanaami et al. |
| 2007/0129705 A1 | 6/2007 | Trombley et al. |
| 2008/0045925 A1 | 2/2008 | Stepovich et al. |
| 2008/0086087 A1* | 4/2008 | Spohn ................. A61M 5/1408 604/151 |
| 2008/0146996 A1 | 6/2008 | Smisson et al. |
| 2009/0069792 A1 | 3/2009 | Frey et al. |
| 2009/0112087 A1 | 4/2009 | Fago |
| 2009/0216192 A1 | 8/2009 | Schriver et al. |
| 2009/0218243 A1 | 9/2009 | Gyrn et al. |
| 2010/0063445 A1 | 3/2010 | Sternberg et al. |
| 2010/0089475 A1 | 4/2010 | Tracey |
| 2010/0091361 A1 | 4/2010 | Yuuki |
| 2010/0114064 A1 | 5/2010 | Kalafut et al. |
| 2010/0286650 A1 | 11/2010 | Fitzgerald |
| 2011/0009826 A1 | 1/2011 | Lewis |
| 2011/0275988 A1 | 11/2011 | Davis et al. |
| 2011/0282196 A1 | 11/2011 | Martz |
| 2012/0020911 A1 | 1/2012 | Seliktar et al. |
| 2012/0101472 A1 | 4/2012 | Schroeder et al. |
| 2012/0178629 A1 | 7/2012 | Hudson et al. |
| 2012/0209111 A1 | 8/2012 | Cowan et al. |
| 2012/0217231 A1 | 8/2012 | Moore et al. |
| 2012/0245560 A1 | 9/2012 | Hochman |
| 2012/0253291 A1 | 10/2012 | Ivosevic et al. |
| 2013/0023048 A1 | 1/2013 | Kim et al. |
| 2013/0030291 A1 | 1/2013 | Lewis |
| 2013/0043273 A1 | 2/2013 | Lee et al. |
| 2013/0053774 A1* | 2/2013 | Kirkpatrick ............ A61M 5/365 604/122 |
| 2013/0204130 A1 | 8/2013 | McArthur et al. |
| 2013/0310756 A1 | 11/2013 | Whalley et al. |
| 2014/0124087 A1 | 5/2014 | Anderson et al. |
| 2014/0276652 A1 | 9/2014 | Gittard |
| 2014/0374353 A1 | 12/2014 | Wright et al. |
| 2015/0260325 A1 | 9/2015 | Quick |
| 2016/0030662 A1 | 2/2016 | Uber, III et al. |
| 2016/0250409 A1 | 9/2016 | Dedig et al. |
| 2017/0035974 A1 | 2/2017 | Berry et al. |
| 2017/0100534 A1 | 4/2017 | Fukikoshi et al. |
| 2017/0165427 A1 | 6/2017 | Uber, III et al. |
| 2017/0232173 A1 | 8/2017 | Perry et al. |
| 2018/0161496 A1 | 6/2018 | Berry et al. |
| 2018/0280630 A1* | 10/2018 | Jiang ................. A61M 5/16809 |
| 2018/0296755 A1 | 10/2018 | Dahlin et al. |
| 2019/0240424 A1 | 8/2019 | Yoshioka et al. |
| 2020/0164141 A1 | 5/2020 | Biermann et al. |
| 2020/0206490 A1 | 7/2020 | Bae |
| 2020/0246541 A1 | 8/2020 | Neftel et al. |
| 2021/0023298 A1 | 1/2021 | McDermott et al. |
| 2021/0146064 A1 | 5/2021 | Knutsson |
| 2021/0193289 A1 | 6/2021 | Cowan et al. |
| 2021/0220561 A1 | 7/2021 | Spohn et al. |
| 2021/0316065 A1 | 10/2021 | Berry et al. |
| 2023/0181816 A1 | 6/2023 | Lee |

FOREIGN PATENT DOCUMENTS

| | | |
|---|---|---|
| EP | 0446898 A2 | 9/1991 |
| EP | 1086661 A2 | 3/2001 |
| EP | 1572266 A2 | 9/2005 |
| EP | 1769849 A1 | 4/2007 |
| EP | 1800704 A1 | 6/2007 |
| EP | 2005934 A2 | 12/2008 |
| EP | 2098258 A1 | 9/2009 |
| EP | 2692375 A1 | 2/2014 |
| EP | 2719420 A1 | 4/2014 |
| EP | 2754459 A1 | 7/2014 |
| EP | 2767299 A1 | 8/2014 |
| EP | 3057648 A1 | 8/2016 |
| EP | 2962770 B1 | 3/2017 |
| EP | 3248635 A1 | 11/2017 |
| FR | 1288915 A | 3/1962 |
| GB | 1173662 A | 12/1969 |
| GB | 2214819 A | 9/1989 |
| GB | 2374143 A | 10/2002 |
| JP | H02-88664 | 7/1990 |
| JP | H0849598 A | 2/1996 |
| JP | H0999034 A | 4/1997 |
| JP | 5485885 B2 | 5/2014 |
| JP | 5511409 B2 | 6/2014 |
| JP | 5882595 B2 | 3/2016 |
| JP | 5897798 B2 | 3/2016 |
| JP | 6552258 B2 | 7/2019 |
| JP | 6839853 B2 | 3/2021 |
| NO | 2021173743 A1 | 9/2021 |
| WO | 9221391 A1 | 12/1992 |
| WO | 9528195 A1 | 10/1995 |
| WO | 9707841 A2 | 3/1997 |
| WO | 0204049 A1 | 1/2002 |
| WO | 02066100 A2 | 8/2002 |
| WO | 2004033023 A1 | 4/2004 |
| WO | 2005035995 A1 | 4/2005 |
| WO | 2007133942 A2 | 11/2007 |
| WO | 2008050218 A2 | 5/2008 |
| WO | 2008153831 A2 | 12/2008 |
| WO | 2009038955 A1 | 3/2009 |
| WO | 2010004206 A2 | 1/2010 |
| WO | 2010014654 A1 | 2/2010 |
| WO | 2011011346 A1 | 1/2011 |
| WO | 2011125303 A1 | 10/2011 |
| WO | 2011129175 A1 | 10/2011 |
| WO | 2012061140 A1 | 5/2012 |
| WO | 2012155035 A1 | 11/2012 |
| WO | 2013043868 A1 | 3/2013 |
| WO | 2013043881 A1 | 3/2013 |
| WO | 2013043889 A1 | 3/2013 |
| WO | 2014027009 A1 | 2/2014 |
| WO | 2014055283 A1 | 4/2014 |
| WO | 2014160326 A1 | 10/2014 |
| WO | 2015058088 A1 | 4/2015 |
| WO | 2015066506 A2 | 5/2015 |
| WO | 2015164783 A1 | 10/2015 |
| WO | 2016058946 A1 | 4/2016 |
| WO | 2016069711 A1 | 5/2016 |
| WO | 2016069714 A1 | 5/2016 |
| WO | 2016112163 A1 | 7/2016 |
| WO | 2016157886 A1 | 10/2016 |
| WO | 2016172467 A1 | 10/2016 |
| WO | 2016190904 A1 | 12/2016 |
| WO | 2016191485 A1 | 12/2016 |
| WO | 2017040154 A1 | 3/2017 |
| WO | 2017091635 A1 | 6/2017 |
| WO | 2017091636 A1 | 6/2017 |
| WO | 2017091643 A1 | 6/2017 |
| WO | 2018053074 A1 | 3/2018 |
| WO | 2018057386 A1 | 3/2018 |
| WO | 2018218132 A1 | 11/2018 |
| WO | 2019046259 A1 | 3/2019 |
| WO | 2019046260 A1 | 3/2019 |
| WO | 2019046299 A1 | 3/2019 |
| WO | 2019152978 A1 | 8/2019 |
| WO | 2019204605 A1 | 10/2019 |
| WO | 2019204617 A1 | 10/2019 |
| WO | 2020055785 A1 | 3/2020 |

(56) References Cited

FOREIGN PATENT DOCUMENTS

| | | |
|---|---|---|
| WO | 2020055818 A1 | 3/2020 |
| WO | 2021050507 A1 | 3/2021 |
| WO | 2021168076 A1 | 8/2021 |
| WO | 2021188416 A1 | 9/2021 |
| WO | 2021188460 A1 | 9/2021 |
| WO | 2021222619 A1 | 11/2021 |
| WO | 2021247595 A1 | 12/2021 |
| WO | 2021257667 A1 | 12/2021 |
| WO | 2021257699 A1 | 12/2021 |
| WO | 2022035791 A1 | 2/2022 |
| WO | 2022036058 A1 | 2/2022 |
| WO | 2022265695 A1 | 12/2022 |

OTHER PUBLICATIONS

The International Preliminary Report on Patentability and Written Opinion dated Sep. 24, 2015 from corresponding PCT Application No. PCT/US2014/022629.

The International Preliminary Report on Patentability and Written Opinion dated Sep. 24, 2015from corresponding PCT Application No. PCT/US2014/026324.

The International Search Report and Written Opinion dated Jul. 18, 2014 from corresponding PCT Application No. PCT/US2014/026324, which was filed on Mar. 13, 2014.

The International Search Report and Written Opinion dated Jul. 30, 2014 from corresponding PCT Application No. PCT/US2014/022629.

International Preliminary Report on Patentability from PCT Application No. PCT/US2021/022321, dated Sep. 29, 2022.

International Preliminary Report on Patentability from PCT Application No. PCT/US2021/035273, dated Dec. 15, 2022.

International Preliminary Report on Patentability from PCT Application No. PCT/US2021/045298, dated Feb. 23, 2023.

International Preliminary Report on Patentability from PCT Application No. PCT/US2021/045689, dated Feb. 23, 2023.

International Preliminary Report on Patentability from PCT Application No. PCT/US2021/061201, dated Jun. 15, 2023.

International Search Report and Written Opinion from PCT Application No. PCT/US2016/063448, dated Feb. 24, 2017.

PCT Application No. PCT/US2023/025159 entitled "Disinfecting Cap For Fluid Path Element", filed Jun. 13, 2023.

Supplementary European Search Report from EP 14770001, dated Nov. 25, 2016.

Un; Haluk, "A New Device Preventing Air Embolism During the Angiography, Air Trap Device: An In-Vitro Experimental Air Emboli Study", Proceedings of the 2019 Design of Medical Devices Conference, 2019.

\* cited by examiner

IN-LINE AIR BUBBLE SUSPENSION APPARATUS FOR ANGIOGRAPHY INJECTOR FLUID PATHS

CROSS-REFERENCE TO RELATED APPLICATIONS

This application is a U.S. national phase application under 35 U.S.C. § 371 of PCT International Application No. PCT/US2021/037623, filed 16 Jun. 2021, and claims the benefit of U.S. Provisional Patent Application No. 62/705,250, filed on 18 Jun. 2020, the disclosures of which are incorporated herein by reference in their entirety.

BACKGROUND OF THE DISCLOSURE

Field of the Disclosure

The present disclosure relates generally to fluid injector systems and associated fluid path elements for high pressure injection of medical fluids. More specifically, the present disclosure describes a fluid delivery system having at least one air bubble suspension apparatus. Other embodiments relate to features of air bubble suspension apparatuses suitable for use in fluid injection procedures.

Description of Related Art

In many medical diagnostic and therapeutic procedures, a medical practitioner, such as a physician, injects a patient with one or more medical fluids. A number of injector-actuated syringes and powered fluid injectors for pressurized injection of medical fluids, such as a contrast solution (often referred to simply as "contrast"), a flushing agent, such as saline or Ringer's lactate, and other medical fluids, have been developed for use in procedures such as cardiovascular angiography (CV), computed tomography (CT), ultrasound, magnetic resonance imaging (MRI), positron emission tomography (PET), and other imaging procedures. In general, these fluid injectors are designed to deliver a preset amount of fluid at a preset pressure and/or flow rate.

Typically, fluid injectors have at least one drive member, such as a piston, that connects to the syringe, for example via connection with a plunger or an engagement feature on a proximal end wall of the syringe. The syringe may include a rigid barrel with the syringe plunger being slidably disposed within the barrel. The drive members drive the plungers in a proximal and/or distal direction relative to a longitudinal axis of the barrel to draw fluid into or deliver the fluid from the syringe barrel. In certain applications, such as angiography, the medical fluids are injected directly into the arterial system at fluid pressures up to 1200 psi.

During certain injection procedures at these high fluid pressures with fluid being administered directly to the cardiac system, it is imperative that no air be co-injected with the medical fluid as patient harm may result. Thus, new methods and devices are necessary to prevent injection of inadvertent air during a high-pressure fluid injection procedure. Further, at pressures of up to 1200 psi during some CV injections, air in the fluid path compresses; however, if the injection is stopped upon air detection, the air volume may expand rapidly due to release of pressure. In addition, release of system compliance upon cessation of injection may result in continued fluid flow as the compliance volume is released in the absence of the fluid pressure. Thus, high pressure fluid injection systems must address for these phenomena when preventing inadvertent air injection.

SUMMARY OF THE DISCLOSURE

In view of the foregoing, there exists a need for devices, systems, and methods for preventing air from being delivered to a patient during an injection procedure. Embodiments of the present disclosure are directed to an apparatus for suspending air bubbles in a fluid path of a fluid injector system. The apparatus includes a housing, an internal chamber having a curved interior wall defined within the housing, an inlet fluid pathway in fluid communication with the internal chamber, the inlet fluid pathway extending into the chamber at a tangent to the curved interior wall, and an outlet fluid pathway in fluid communication with the internal chamber, the outlet fluid pathway spaced from the inlet fluid pathway such that fluid flowing into the internal chamber via the inlet fluid pathway is directed away from the outlet fluid pathway. The internal chamber is configured to create an internal fluid vortex in an injection fluid entering the internal chamber from the inlet fluid pathway, and wherein the internal fluid vortex at least temporarily suspends one or more air bubbles in the fluid in the internal vortex and delays the passage of the one or more air bubbles to the outlet fluid pathway.

In some embodiments, the outlet fluid pathway extends from the internal chamber in a direction perpendicular to a flow path of fluid within the internal chamber.

In some embodiments, at least a portion of the outlet fluid pathway has a cross-sectional area greater than a cross-sectional area of the inlet fluid pathway to reduce fluid velocity in the outlet fluid pathway relative to fluid velocity in the inlet fluid pathway.

In some embodiments, the outlet fluid pathway extends substantially parallel to the inlet fluid pathway. In some embodiments, the internal chamber is at least partly spherical or hemispherical.

In some embodiments, the apparatus further includes a recess extending radially outward from the internal chamber.

In some embodiments, the apparatus further includes a valve in fluid communication with the internal chamber for draining air accumulated in the internal chamber.

In some embodiments, the housing includes a first housing section including the inlet fluid pathway and the outlet fluid pathway, and a second housing section including at least a portion of the internal chamber. One of the first housing section and the second housing section includes a flange for receiving the other of the first housing section and second housing section.

In some embodiments, the housing includes at least one strengthening rib extending radially outward from the outlet fluid pathway.

In some embodiments, the apparatus further includes a screen disposed in the outlet fluid pathway such that fluid flowing out of the internal chamber passes through the screen.

In some embodiments, the housing includes a light-transmissible material configured to illuminate air bubbles in the internal chamber.

In some embodiments, the housing includes a connector arm configured for attachment to an injector housing of the fluid injector system.

In some embodiments, the apparatus further includes an adjustable valve for changing a cross-sectional area of at least one of the inlet fluid pathway and outlet fluid pathway.

Other embodiment of the present disclosure are directed to an apparatus for suspending air bubbles in a fluid path of a fluid injector system. The apparatus includes a housing defining an internal chamber, an inlet fluid pathway in fluid communication with the internal chamber, an outlet fluid pathway in fluid communication with the internal chamber; and an extension tube in fluid communication with the inlet fluid pathway and extending into the internal chamber. The extension tube includes a tip spaced apart from the outlet fluid pathway such that fluid flowing into the internal chamber via the extension tube is directed away from the outlet fluid pathway.

In some embodiments, the apparatus further includes a screen dividing the internal chamber into an inlet portion and an outlet portion. The screen includes at least one aperture providing fluid communication between the inlet portion and the outlet portion. Fluid flowing into the internal chamber from the extension tube must flow through the at least one aperture of the screen to reach the outlet fluid pathway.

In some embodiments, a first portion of the screen adjacent to the tip of the extension tube is impermeable to fluid, and a second portion of the screen adjacent to the outlet fluid pathway includes the at least one aperture. In some embodiments, the screen includes a funnel defining the at least one aperture, the funnel tapering from a maximum cross-sectional area adjacent the inlet portion of the internal chamber to a minimum diameter extending into the outlet portion of the internal chamber.

In some embodiments, the screen includes a hood at least partially obstructing the at least one aperture such that fluid must flow around the hood to flow through the at least one aperture. In some embodiments, the screen includes mesh. In some embodiments, the at least one aperture includes two or more apertures arranged in an arc.

In some embodiments, the housing includes a first housing section including a flange configured to receive the screen, and a second housing section received within the flange of the first housing section to capture the screen between the first housing section and the second housing section.

In some embodiments, the inlet fluid pathway tapers from a smaller cross-sectional area to a larger cross-sectional area in a direction of fluid flow through the inlet fluid pathway to reduce flow velocity of fluid flowing through the inlet fluid pathway.

In some embodiments, the extension tube extends parallel to an inner wall of the internal chamber. In some embodiments, the outlet fluid pathway extends at an acute angle relative to the inlet fluid pathway.

In some embodiments, the housing includes a light-transmissible material configured to illuminate air bubbles in the internal chamber.

In some embodiments the housing includes a connector arm configured for attachment to an injector housing of the fluid injector system.

In some embodiments, the apparatus further includes an adjustable valve for changing a cross-sectional area of at least one of the inlet fluid pathway and outlet fluid pathway.

Other embodiments of the present disclosure are direct to a fluid injector system including at least one fluid reservoir configured for injecting medical fluid and at least one bubble suspension apparatus in fluid communication with the at least one fluid reservoir. The at least one bubble suspension apparatus includes a housing defining an internal chamber, an inlet fluid pathway in fluid communication with the internal chamber, and an outlet fluid pathway in fluid communication with the internal chamber, the outlet fluid pathway spaced from the inlet fluid pathway such that fluid flowing into the internal chamber via the inlet fluid pathway is directed away from the outlet fluid pathway. The fluid injector system further includes at least one air detector configured to detect one or more air bubbles in a fluid path connecting the at least one fluid reservoir to the at least one bubble suspension apparatus, and at least one shutoff valve downstream of the at least one bubble suspension apparatus and configured to move from an open position to a closed position in response to the air detector detecting the one or more air bubbles in the fluid path. The internal chamber is configured to create an internal fluid vortex in an injection fluid entering the internal chamber from the inlet fluid pathway, and wherein the internal fluid vortex at least temporarily suspends one or more air bubbles in the fluid in the internal vortex and delays the passage of the one or more air bubbles to the outlet fluid pathway. Features of the various embodiments of the bubble suspension apparatus suitable for use with fluid injector systems are described herein.

In some embodiments, the bubble suspension apparatus is movable between an injection position in which the outlet fluid pathway extends substantially vertically downward from the internal chamber such that buoyancy of air bubbles in the internal chamber further induces the one or more air bubbles to remain suspended in the internal fluid vortex in the internal chamber, and a priming position in which the outlet fluid pathway extends substantially vertically upward from the chamber such that the buoyancy of air bubbles in the internal chamber induces the air bubbles to flow from the internal fluid vortex through the outlet fluid pathway.

In some embodiments, the system further including an adjustable valve for changing a cross-sectional area of at least one of the inlet fluid pathway and the outlet fluid pathway.

Further aspects or examples of the present disclosure are described in the following numbered clauses:

Clause 1. An apparatus for suspending air bubbles in a fluid path of a fluid injector system, the apparatus comprising: a housing; an internal chamber having a curved interior wall defined within the housing; an inlet fluid pathway in fluid communication with the internal chamber, the inlet fluid pathway extending into the chamber at a tangent to the curved interior wall; and an outlet fluid pathway in fluid communication with the internal chamber, the outlet fluid pathway spaced from the inlet fluid pathway such that fluid flowing into the internal chamber via the inlet fluid pathway is directed away from the outlet fluid pathway, wherein the internal chamber is configured to create an internal fluid vortex in an injection fluid entering the internal chamber from the inlet fluid pathway, and wherein the internal fluid vortex at least temporarily suspends one or more air bubbles in the fluid in the internal vortex and delays the passage of the one or more air bubbles to the outlet fluid pathway.

Clause 2. The apparatus according to clause 1, wherein the outlet fluid pathway extends from the internal chamber in a direction perpendicular to a flow path of fluid within the internal chamber.

Clause 3. The apparatus according to clause 1 or 2, wherein at least a portion of the outlet fluid pathway has a cross-sectional area greater than a cross-sectional area of the inlet fluid pathway to reduce fluid velocity in the outlet fluid pathway relative to fluid velocity in the inlet fluid pathway.

Clause 4. The apparatus according to any of clauses 1-3, wherein the outlet fluid pathway extends substantially parallel to the inlet fluid pathway.

Clause 5. The apparatus according to any of clauses 1-4, wherein the internal chamber is at least partly spherical or hemispherical.

Clause 6. The apparatus according to any of clauses 1-5, further comprising a recess extending radially outward from the internal chamber.

Clause 7. The apparatus according to any of clauses 1-6, further comprising a valve in fluid communication with the internal chamber for draining air accumulated in the internal chamber.

Clause 8. The apparatus according to any of clauses 1-7, wherein the housing comprises: a first housing section comprising the inlet fluid pathway and the outlet fluid pathway; and a second housing section comprising at least a portion of the internal chamber, wherein one of the first housing section and the second housing section comprises a flange for receiving the other of the first housing section and the second housing section.

Clause 9. The apparatus according to any of clauses 1-8, wherein the housing comprises at least one strengthening rib extending radially outward from the outlet fluid pathway.

Clause 10. The apparatus according to any of clauses 1-9, further comprising a screen disposed in the outlet fluid pathway such that fluid flowing out of the internal chamber passes through the screen.

Clause 11. The apparatus according to any of clauses 1-10, wherein the housing comprises a light-transmissible material configured to illuminate air bubbles in the internal chamber.

Clause 12. The apparatus according to any of clauses 1-11, wherein the housing comprises a connector arm configured for attachment to an injector housing of the fluid injector system.

Clause 13. The apparatus according to any of clauses 1-12, further comprising an adjustable valve for changing a cross-sectional area of at least one of the inlet fluid pathway and the outlet fluid pathway.

Clause 14. An apparatus for suspending air bubbles in a fluid path of a fluid injector system, the apparatus comprising: a housing defining an internal chamber; an inlet fluid pathway in fluid communication with the internal chamber; an outlet fluid pathway in fluid communication with the internal chamber; and an extension tube in fluid communication with the inlet fluid pathway and extending into the internal chamber, the extension tube comprising a tip spaced apart from the outlet fluid pathway such that fluid flowing into the internal chamber via the extension tube is directed away from the outlet fluid pathway.

Clause 15. The apparatus according to clause 14, further comprising a screen dividing the internal chamber into an inlet portion and an outlet portion, wherein the screen comprises at least one aperture providing fluid communication between the inlet portion and the outlet portion, and wherein fluid flowing into the internal chamber from the extension tube must flow through the at least one aperture of the screen to reach the outlet fluid pathway.

Clause 16. The apparatus according to clause 14 or 15, wherein a first portion of the screen adjacent to the tip of the extension tube is impermeable to fluid, and wherein a second portion of the screen adjacent to the outlet fluid pathway comprises the at least one aperture.

Clause 17. The apparatus according to any of clauses 14-16, wherein the screen comprises a funnel defining the at least one aperture, the funnel tapering from a maximum cross-sectional area adjacent the inlet portion of the internal chamber to a minimum diameter extending into the outlet portion of the internal chamber.

Clause 18. The apparatus according to any of clauses 14-17, wherein the screen comprises a hood at least partially obstructing the at least one aperture such that fluid must flow around the hood to flow through the at least one aperture.

Clause 19. The apparatus according to any of clauses 14-18, wherein the screen comprises mesh.

Clause 20. The apparatus according to any of clauses 14-19, wherein the at least one aperture comprises two or more apertures arranged in an arc.

Clause 21. The apparatus according to any of clauses 14-20, wherein the housing comprises: a first housing section comprising a flange configured to receive the screen; and a second housing section received within the flange of the first housing section to capture the screen between the first housing section and the second housing section.

Clause 22. The apparatus according to any of clauses 14-21, wherein the inlet fluid pathway tapers from a smaller cross-sectional area to a larger cross-sectional area in a direction of fluid flow through the inlet fluid pathway to reduce flow velocity of fluid flowing through the inlet fluid pathway.

Clause 23. The apparatus according to any of clauses 14-22, wherein the extension tube extends parallel to an inner wall of the internal chamber.

Clause 24. The apparatus according to any of clauses 14-23, wherein the outlet fluid pathway extends at an acute angle relative to the inlet fluid pathway.

Clause 25. The apparatus according to any of clauses 14-24, wherein the housing comprises a light-transmissible material configured to illuminate air bubbles in the internal chamber.

Clause 26. The apparatus according to any of clauses 14-25, wherein the housing comprises a connector arm configured for attachment to an injector housing of the fluid injector system.

Clause 27. The apparatus according to any of clauses 14-26, further comprising an adjustable valve for changing a cross-sectional area of at least one of the inlet fluid pathway and the outlet fluid pathway.

Clause 28. A fluid injector system comprising: at least one fluid reservoir configured for injecting medical fluid; at least one bubble suspension apparatus in fluid communication with the at least one fluid reservoir; the at least one bubble suspension apparatus comprising: a housing defining an internal chamber; an inlet fluid pathway in fluid communication with the internal chamber; and an outlet fluid pathway in fluid communication with the internal chamber, the outlet fluid pathway spaced from the inlet fluid pathway such that fluid flowing into the internal chamber via the inlet fluid pathway is directed away from the outlet fluid pathway; at least one air detector configured to detect one or more air bubbles in a fluid path connecting the at least one fluid reservoir to the at least one bubble suspension apparatus; and at least one shutoff valve downstream of the at least one bubble suspension apparatus and configured to move from an open position to a closed position in response to the air detector detecting the one or more air bubbles in the fluid path, wherein the internal chamber is configured to create an internal fluid vortex in an injection fluid entering the internal chamber from the inlet fluid pathway, and wherein the internal fluid vortex at least temporarily suspends one or more air bubbles in the fluid in the internal vortex and delays the passage of the one or more air bubbles to the outlet fluid pathway.

Clause 29. The fluid injector system according to clause 28, wherein the bubble suspension apparatus is movable between: an injection position in which the outlet fluid pathway extends substantially vertically downward from the internal chamber such that buoyancy of air bubbles in the internal chamber further induces the one or more air bubbles to remain suspended in the internal fluid vortex in the internal chamber; and a priming position in which the outlet fluid pathway extends substantially vertically upward from the chamber such that the buoyancy of air bubbles in the internal chamber induces the air bubbles to flow from the internal fluid vortex through the outlet fluid pathway.

Clause 30. The fluid injector system according to clause 28 or 29, wherein the internal chamber comprises at least one curved interior wall, wherein the inlet fluid pathway extends into the internal chamber at a tangent to the curved interior wall.

Clause 31. The fluid injector system according to any of clauses 28-30, wherein the outlet fluid pathway extends from the internal chamber in a direction substantially perpendicular to a flow path of fluid in the internal fluid vortex within the internal chamber.

Clause 32. The fluid injector system according to any of clauses 28-31, wherein at least a portion of the outlet fluid pathway has a cross-sectional area greater than a cross-sectional area of the inlet fluid pathway to reduce fluid velocity in the outlet fluid pathway relative to fluid velocity in the inlet fluid pathway.

Clause 33. The fluid injector system according to any of clauses 28-32, wherein the outlet fluid pathway extends substantially parallel to the inlet fluid pathway.

Clause 34. The fluid injector system according to any of clauses 28-33, wherein the internal chamber is at least partially spherical or hemispherical.

Clause 35. The fluid injector system according to any of clauses 28-34, wherein the bubble suspension apparatus further comprises a recess extending radially outward from the internal chamber in a direction substantially opposite the outlet fluid pathway.

Clause 36. The fluid injector system according to any of clauses 28-35, further comprising a valve on the recess and in fluid communication with the internal chamber for draining air accumulated in the recess.

Clause 37. The fluid injector system according to any of clauses 28-36, wherein the housing of the bubble suspension apparatus comprises: a first housing section comprising at least one of the inlet fluid pathway and the outlet fluid pathway; and a second housing section comprising at least a portion of the internal chamber, wherein one of the first housing section and the second housing section comprises a flange for receiving the other of the first housing section and the second housing section.

Clause 38. The fluid injector system according to any of clauses 28-37, wherein the housing of the bubble suspension apparatus comprises at least one strengthening rib extending radially outward from outlet fluid pathway.

Clause 39. The fluid injector system according to any of clauses 28-38, wherein the bubble suspension apparatus further comprises a screen disposed proximal to the outlet fluid pathway such that fluid flowing out of the internal chamber passes through the screen.

Clause 40. The fluid injector system according to any of clauses 28-39, wherein one or more of the one or more air bubbles temporarily adhere to a surface of the screen as the fluid passes through the screen.

Clause 41. The fluid injector system according to any of clauses 28-40, wherein the screen comprises a hydrophilic coating on at least a portion of a surface of the screen.

Clause 42. The fluid injector system according to any of clauses 28-41, wherein the bubble suspension apparatus further comprises an extension tube in fluid communication with the inlet fluid pathway and extending into the internal chamber, the extension tube comprising a tip spaced apart from the outlet fluid pathway such that fluid flowing into the internal chamber via the extension tube is directed away from the outlet fluid pathway.

Clause 43. The fluid injector system according to any of clauses 28-42, wherein the screen divides the internal chamber into an inlet portion and an outlet portion, wherein the screen comprises at least one aperture providing fluid communication between the inlet portion and the outlet portion, and wherein fluid flowing into the internal chamber from the inlet fluid pathway must flow through the at least one aperture of the screen to reach the outlet fluid pathway.

Clause 44. The fluid injector system according to any of clauses 28-43, wherein a first portion of the screen adjacent to the tip of the extension tube is impermeable to fluid, and wherein a second portion of the screen adjacent to the outlet fluid pathway comprises the at least one aperture.

Clause 45. The fluid injector system according to any of clauses 28-44, wherein the screen comprises a funnel defining the at least one aperture, the funnel tapering from a maximum cross-sectional area adjacent the inlet portion of the internal chamber to a minimum diameter extending into the outlet portion of the internal chamber.

Clause 46. The fluid injector system according to any of clauses 28-45, wherein the screen comprises a hood at least partially obstructing the at least one aperture such that fluid must flow around the hood to flow through the at least one aperture.

Clause 47. The fluid injector system according to any of clauses 28-46, wherein the screen comprises mesh.

Clause 48. The fluid injector system according to any of clauses 28-47, wherein the at least one aperture comprises two or more apertures arranged in an arc.

Clause 49. The fluid injector system according to any of clauses 28-48, wherein the bubble suspension apparatus delays passage of the one or more air bubbles to the outlet fluid pathway by at least 100 milliseconds.

Clause 50. The fluid injector system according to any of clauses 28-49, wherein the housing comprises: a first housing section comprising a flange configured to receive the screen; a second housing section received within the flange of the first housing section to capture the screen between the first housing section and the second housing section.

Clause 51. The fluid injector system according to any of clauses 28-50, wherein the inlet fluid pathway tapers from a smaller cross-sectional area to a larger cross-sectional area in a direction of fluid flow through the inlet fluid pathway to reduce flow velocity of fluid flowing through the inlet fluid pathway.

Clause 52. The fluid injector system according to any of clauses 28-51, wherein the extension tube extends parallel to an inner wall of the internal chamber.

Clause 53. The fluid injector system according to any of clauses 28-52, wherein the outlet fluid pathway extends at an acute angle relative to the inlet fluid pathway.

Clause 54. The fluid injector system according to any of clauses 28-53, wherein the housing of the bubble suspension apparatus comprises a light-transmissible material configured to illuminate air bubbles in the internal chamber.

Clause 55. The fluid injector system according to any of clauses 28-54, wherein the housing of the bubble suspension apparatus comprises a connector arm configured for attachment to an injector housing of the fluid injector system.

Clause 56. The fluid injector system according to any of clauses 28-55, further comprising an adjustable valve for changing a cross-sectional area of at least one of the inlet fluid pathway and the outlet fluid pathway.

Further details and advantages of the various examples described in detail herein will become clear upon reviewing the following detailed description of the various examples in conjunction with the accompanying drawing figures.

BRIEF DESCRIPTION OF THE DRAWINGS

Referring to the drawings in which like reference characters refer to like parts throughout the several views thereof, the present disclosure is generally directed to an in-line air bubble suspension apparatus for use with a fluid injector system.

DETAILED DESCRIPTION

Figure 1:
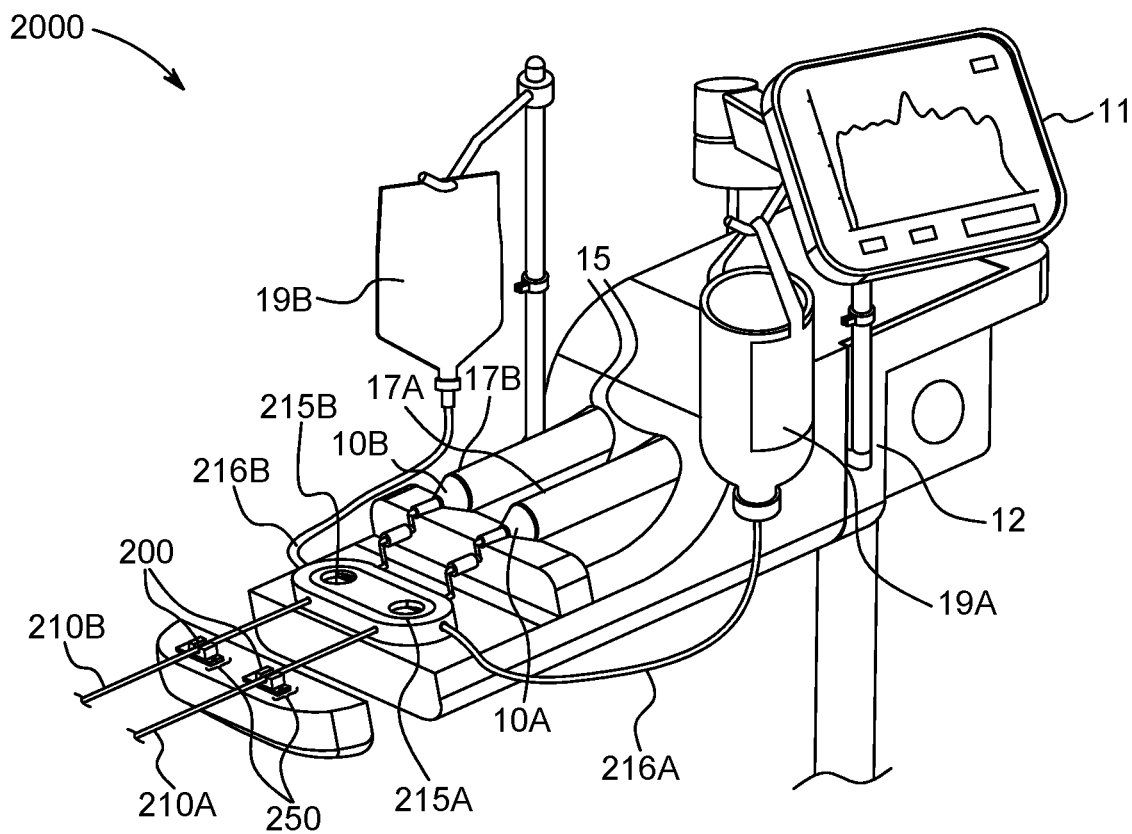
FIG. 1 is a perspective view of a fluid injector system according to an embodiment of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. Spatial or directional terms, such as "left", "right", "inner", "outer", "above", "below", and the like, are not to be considered as limiting as the invention can assume various alternative orientations.

As used herein, the singular form of "a", "an", and "the" include plural referents unless the context clearly dictates otherwise. All numbers used in the specification and claims are to be understood as being modified in all instances by the term "about". The terms "approximately", "about", and "substantially" mean a range of plus or minus ten percent of the stated value.

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more of B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

It is also to be understood that the specific devices and processes illustrated in the attached drawings, and described in the following specification, are simply exemplary examples of the disclosure. Hence, specific dimensions and other physical characteristics related to the examples disclosed herein are not to be considered as limiting.

When used in relation to a component of a fluid delivery system such as a fluid reservoir, a syringe, an air suspension apparatus, or a fluid line, the term "distal" refers to a portion of said component nearest to a patient. When used in relation to a component of an injector system such as a fluid reservoir, a syringe, an air suspension apparatus, or a fluid line, the term "proximal" refers to a portion of said component nearest to the injector of the injector system (i.e. the portion of said component farthest from the patient). When used in relation to a component of a fluid delivery system such as a fluid reservoir, a syringe, an air suspension apparatus, or a fluid line, the term "upstream" refers to a direction away from the patient and towards the injector of the injector system. For example, if a first component is referred to as being "upstream" of a second component, the first component is located nearer to the injector than the second component is to the injector. When used in relation to a component of a fluid delivery system such as a fluid reservoir, a syringe, an air suspension apparatus, or a fluid line, the term "downstream" refers to a direction towards the patient and away from the injector of the fluid delivery system. For example, if a first component is referred to as being "downstream" of a second component, the first component is located nearer to the patient than the second component is to the patient.

As used herein, the terms "capacitance" and "impedance" are used interchangeably to refer to a volumetric expansion of injector components, such as fluid reservoirs, syringes, fluid lines, and/or other components of a fluid delivery system as a result of pressurized fluids with such components and/or uptake of mechanical slack by force applied to components. Capacitance and impedance may be due to high injection pressures, which may be on the order of 1,200 psi in some angiographic procedures, and may result in a volume of fluid held within a portion of a component in excess of the desired quantity selected for the injection procedure or the resting volume of the component. Additionally, capacitance of various components can, if not properly accounted for, adversely affect the accuracy of pressure sensors of the injector system because the volumetric expansion of components can cause an artificial drop in measured pressure of those components.

The terms "first", "second", and the like are not intended to refer to any particular order or chronology, but refer to different conditions, properties, or elements. All documents referred to herein are "incorporated by reference" in their entirety. The term "at least" is synonymous with "greater than or equal to". The term "not greater than" is synonymous with "less than or equal to".

It is to be understood that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

While the systems and apparatuses described herein are with reference to an angiography (CV) injection system, other pressurized injection protocols, such as computed tomography (CT), ultrasound, positron emission tomography (PET), and magnetic resonance imaging (MRI) may also incorporate the various embodiments described herein for preventing injection of air.

Referring to the drawings in which like reference characters refer to like parts throughout the several views thereof, the present disclosure is generally directed to fluid injector systems and bubble suspension apparatuses for delaying movement of one or more air bubbles through a fluid line towards a patient and preventing the delivery of the one or more air bubbles that may inadvertently occur during an injection procedure.

Referring first to FIG. 1, an embodiment of a dual syringe angiography injector system 2000 is illustrated. The angiography injector system 2000 is configured for injection of two medical fluids through a first fluid path 210A for a medical fluid, such as an imaging contrast media for an angiography injection procedure, and a second fluid path 210B for a flushing fluid, such as saline or Ringer's lactate. The dual syringe angiography injector system 2000 may include an injector housing 12 having two syringe ports 15 configured to engage two syringes 10A, 10B. In some embodiments, the syringes 10A, 10B may be retained within corresponding pressure jackets 17A, 17B for example to prevent pressure-induced swelling and potential bursting of the syringes 10A, 10B.

The fluid injector system 2000 may further include at least one graphical user interface (GUI) 11 through which an operator can view and control the status of an injection procedure. The GUI 11 may be in operative communication with a controller 900 (see FIG. 2) which sends and receives commands between the GUI 11 and fluid injector system 2000. The GUI 11 may be provided on the injector housing 12 or may be mounted remotely from the injector housing 12.

The dual syringe angiography injector system 2000 may further include at least one upstream air detector 200 associated with fluid paths 210A,B for detecting one or more air bubbles within an air detection tubing region 250 of the first fluid path 210A and the second fluid path 210B. The air detection tubing region 250, for example, may be associated with a proximal or upstream portion of the first fluid path 210A and the second fluid path 210B. In some embodiments, the at least one air detector 200 may be a single module having at least one sensor operatively associated with each of the first fluid path 210A and the second fluid path 210B. In some embodiments, the at least one air detector 200 may include at least two distinct modules, each module operatively associated with one of the first fluid path 210A and the second fluid path 210B. The at least one air detector 200 may be in operative communication with the controller 900 (see FIG. 2) such that the controller 900 may receive signals from the at least one air detector 200 indicating the detection of one or more air bubbles in one or both of the first fluid path 210A and/or the second fluid path 210B. Once the signal(s) are received, controller 900 may send a signal or command to the fluid injector 2000 to stop a fluid injection procedure, for example, by closing one or more shut-off valves (see FIG. 2, 215A, 215B and/or 390) downstream of the at least one air detector 200 to prevent the detected air bubble from being injected into the patient. The at least one air detector 200 may include an ultrasonic sensor, and optical sensor, or other suitable sensor arrangement, configured to detect the one or more air bubbles within the fluid path.

With continued reference to FIG. 1, the dual syringe angiography injector system 2000 may further include bulk fluid containers 19A and 19B for filling and refilling the respective syringes 10A, 10B with imaging contrast media and flushing fluid, respectively. The bulk fluid containers 19A and 19B may be in selective fluid communication with the syringes 10A, 10B via respective bulk fluid paths 216A and 216B and bulk fluid valves 215A and 215B.

Further details and examples of suitable nonlimiting powered injector systems, including syringes, pressure jackets and pressure jacket retention mechanisms, tubing, shut-off valves, controllers, and air detectors, are described in U.S. Pat. Nos. 5,383,858; 7,553,294; 7,666,169; 8,945,051; 10,022,493; and 10,507,319, and International PCT Application Nos. PCT/US2013/061275; PCT/US2018/034613; PCT/US2020/049885; PCT/US2021/035273; and PCT/US2021/029963, the disclosures of which are hereby incorporated by reference in their entireties. While the fluid injection system 2000 is described herein in the context of a dual syringe angiography (CV) injector, it is to be understood that the fluid injector system 2000 may be adapted for single- and multiple-syringe configurations of any injection procedure (e.g. CT, PET, MRI, ultrasound, etc.)

Figure 2:
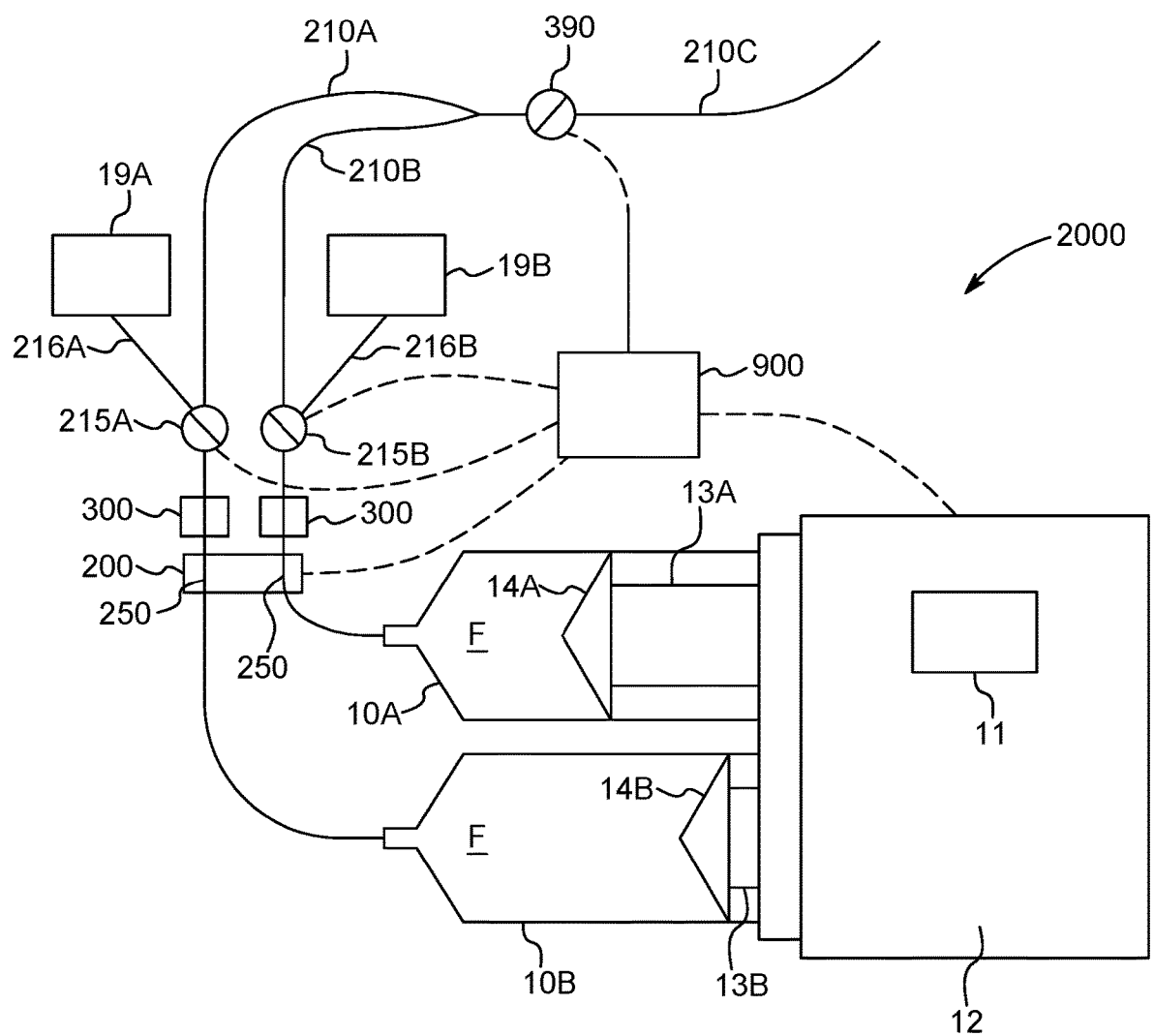
FIG. 2 is a schematic view of a fluid injector system in accordance with an embodiment of the present disclosure.

Referring now to FIG. 2, a schematic diagram of the fluid injector system 2000 shown in FIG. 1 is illustrated. The injector system 2000 includes a piston 13A, 13B respectively associated with each of the syringes 10A, 10B and their corresponding pressure jackets 17A, 17B (see FIG. 1). Each of the pistons 13A, 13B is configured to drive a respective plunger 14A, 14B within a barrel of the respective syringe 10A, 10B. The controller 900 is operatively associated with the injector system 2000, for example to activate the pistons 13A, 13B to reciprocatively move the plungers 14A, 14B within the syringes 10A, 10B and thereby execute and halt an injection procedure. In particular, the controller 900 may include at least one processor programmed or configured to actuate the pistons 13A, 13B and various other components of the injector system 2000, such as one or more shut-off valves, as described herein, to take in and deliver medical fluids according to a programmed protocol for an injection procedure. Controller 900 may include computer readable media, such as memory, on which one or more injection protocols may be stored for execution by at least one processor.

The controller 900 may be programmed or configured to execute a filling operation during which the piston 13A, 13B associated with each syringe 10A, 10B is withdrawn toward a proximal end of the syringe 10A, 10B to draw injection fluid F (e.g. imaging contrast media and flushing fluid) into the syringe 10A, 10B from the bulk fluid containers 19A, 19B. During such filling operation, the controller 900 may be programmed or configured to selectively actuate the bulk fluid valves 215A and 215B to establish fluid communication between the respective syringes 10A, 10B and the bulk fluid containers 19A, 19B via the bulk fluid paths 216A and 216B to control filling of the syringes 10A, 10B with the appropriate injection fluid F. Upon completion of the filling operation, and optionally a priming operation to remove any air from the syringes 10A, 10B and various embodiments of the bubble suspension apparatuses described herein (for example by priming any such air back into the bulk fluid containers 19A, 19B or through a priming tube), controller 900 may be programmed or configured to selectively actuate bulk fluid valves 215A and 215B to block fluid communication between the respective syringes 10A, 10B and bulk fluid containers 19A, 19B via bulk fluid paths 216A and 216B.

After the filling operation and priming operation, the controller 900 may be programmed or configured to execute a delivery operation during which the piston 13A, 13B associated with one or both of the syringes 10A, 10B is moved toward a distal end of the syringe to inject injection fluid F into the first fluid path 210A and the second fluid path 210B. The controller 900 may be programmed or configured to selectively actuate the bulk fluid valves 215A and 215B to establish fluid communication between the syringes 10A, 10B and the patient, via the fluid paths 210A, 210B. The first fluid path 210A and the second fluid path 210B ultimately merge into a patient fluid line 210C in fluid communication with the vasculature of the patient. According to various embodiments, the first fluid path 210A and the second fluid path 210B may merge at a fluid mixing connector that provides turbulent mixing of the first fluid and the second fluid, such as a fluid mixing connector described in International PCT Application Nos. PCT/US2021/019507 and PCT/US2014/026324, the disclosures of which are incorporated herein by reference.

The controller 900 may be in operative communication with the at least one air detector 200 such that the controller 900 may stop actuation of the pistons 13A, 13B in response to the air detector 200 detecting the presence of one or more air bubbles in at least one of the first fluid path 210A and/or the second fluid path 210B. The controller 900 may further be in operative communication with at least one downstream automated shutoff valve 390 such that the controller 900 may actuate the at least one downstream shutoff valve 390 to stop fluid flow through the at least one downstream shutoff valve 390 and into the patient vascular system. The at least one downstream shutoff valve 390 may be actuated by the controller 900 between various positions such as an open position in which medical fluid may flow to the patient, a closed position in which fluid flow to the patient is prevented, and a hemodynamic monitoring position in which the vasculature of the patient is in fluid communication with a pressure transducer and isolated from the syringes 10A, 10B. In some embodiments, the downstream shutoff valve 390 may be a stopcock, pinch valve or the like. In certain embodiments, the downstream shutoff valves 390 may be associated with each of the fluid paths 210A and 210B and may be located before the first fluid path 210A and the second fluid path 210B merge into a patient fluid line 210C. Suitable examples of pinch valves and pinch valve/ fluid path configurations are described in International PCT Application No. PCT/US2021/029963. During a normal delivery operation, the controller 900 may be programmed or configured to move the downstream shutoff valve 390 to the open position to establish fluid communication between the patient and the fluid paths 210A, 210B. The controller 900 may be programmed or configured to move the downstream shutoff valve 390 to the closed position in response to air being detected by the at least one air detector 200. Movement of pistons 13A, 13B may also be stopped in response to air being detected by the at least one air detector 200. In the stop position, the downstream shutoff valve 390 fluidly isolates the patient from the fluid paths 210A, 210B, thereby preventing air from being injected into the patient.

With continued reference to FIG. 2, in some embodiments, each of the first fluid path 210A and the second fluid path 210B may include an air bubble suspension apparatus 300 configured to at least temporarily suspend or delay one or more air bubbles flowing through the fluid paths 210A, 210B. Each air bubble suspension apparatus 300 may be provided in line with the associated fluid paths 210A, 210B between the at least one air detector 200 and the downstream shutoff valve 390, such that all fluid flow through the fluid paths 210A, 210B must pass through at least one air bubble suspension apparatus 300 in order to reach the patient.

In some embodiments, the controller 900 may be programmed or configured to move the bulk fluid valves 215A, 215B and/or the downstream shutoff valve 390 to the closed position in response to one or more air bubbles being detected by the at least one air detector 200 along with concomitant stopping of pistons 13A, 13B. In the absence of the air bubble suspension apparatuses 300, the one or more air bubbles detected by the at least one air detector 200 may travel through the fluid paths 210A, 210B at a sufficient velocity to flow past the bulk fluid valves 215A, 215B and the downstream shutoff valve 390 before the bulk fluid valves 215A, 215B and/or the downstream shutoff valve 390 reach the closed position. For example, during a high pressure (e.g., 1200 psi) CV injection procedure, it may take from 60 milliseconds to 90 milliseconds, for example in one embodiment approximately 80 milliseconds, for the injector system 2000 to stop an injection procedure after an air bubble flows into the detection region of the at least one air detector 200. The time required to stop the injection procedure may include: a time required for the at least one air detector 200 to communicate to the controller 900 that an air bubble has been detected, a time required for the controller 900 to communicate with the bulk fluid valves 215A, 215B and/or the downstream shutoff valve 390, and the time required for the bulk fluid valves 215A, 215B and/or the shutoff valve 390 to move from the open position to the closed position. At the high injection pressures (e.g. 1200 psi) typical of CV injection procedures, an air bubble may move from 2.8 mL to 3.6 mL of the volume of the fluid path 210A, 210B over the 60 milliseconds to 90 milliseconds between detection of the air bubble and closure of the bulk fluid valves 215A, 215B and/or the downstream shutoff valve 390. For example, at approximately 1200 psi, an air bubble may travel a distance corresponding to 3.2 mL over 80 milliseconds at a flow rate of 30 mL/sec in a tubing with a 0.072 inch ID. The distance equivalence of 3.2 mL volume for such an embodiment may be approximately 4 feet of tubing length travelled during 80 milliseconds. Thus, even with a rapid response time of the at least one air detector 200, the controller 900, and the bulk fluid valves 215A, 215B and/or the downstream shutoff valve 390, an air bubble may travel a significant distance, potentially into the patient, before the bulk fluid valves 215A, 215B and/or the downstream shutoff valve 390 can be closed. Further, due to the compressibility of a gas compared to a liquid, the air bubble volume may be significantly reduced under the high injection pressures. Only halting fluid flow by stopping pistons 13A, 13B releases pressure on the system allowing the air bubble to expand in volume. The increased volume may move the air bubble down the fluid path past the bulk fluid valves 215A, 215B and/or the downstream shutoff valve 390 before such valves are closed.

Embodiments of the air bubble suspension apparatuses 300 of the present disclosure are configured to at least temporarily delay the flow of air bubbles in the fluid paths 210A, 210B such that the controller 900 has sufficient time to move the bulk fluid valves 215A, 215B and/or the downstream shutoff valve 390 to the closed position prior to the air bubbles reaching the bulk fluid valves 215A, 215B and/or the downstream shutoff valve 390. As noted herein, during a high pressure (e.g., 1200 psi) CV injection procedure, it may take from 60 milliseconds to 90 milliseconds, for example in one embodiment approximately 80 milliseconds, for the system 2000 to close the bulk fluid valves 215A, 215B and/or the downstream shutoff valve 390 in response to the at least one air detector 200 detecting an air bubble in the fluid paths 210A, 210B. Embodiments of the air bubble suspension apparatuses 300 may be configured to delay the flow of air bubbles by at least 60 milliseconds to 90 milliseconds, for example in one embodiment at least 80 milliseconds, so that the bulk fluid valves 215A, 215B and/or the downstream shutoff valve 390 can be moved to the closed position before the air bubble can reach the bulk fluid valves 215A, 215B and/or the downstream shutoff valve 390. As such, the air bubble cannot flow downstream of the bulk fluid valves 215A, 215B and/or the downstream shutoff valve 390 and into the patient. In some embodiments, the controller 900 is programmed or configured to move one or both of the bulk fluid valves 215A, 215B to the closed position in response to the at least one air detector 200 detecting an air bubble in the fluid paths 210A, 210B. In some embodiments, the controller 900 is programmed or configured to move the downstream shutoff valve 390 to the closed position in response to the at least one air detector 200 detecting an air bubble in the fluid paths 210A, 210B. In some embodiments, the controller 900 is programmed or configured to move one or both of the bulk fluid valves 215A, 215B and the downstream shutoff valve 390 to the closed position in response to the at least one air detector 200 detecting an air bubble in the fluid paths 210A, 210B Referring to FIGS. 3-25, features of various embodiments of the air bubble suspension apparatus 300 are shown according to the present disclosure. In general, embodiments of the air bubble suspension apparatus 300 includes a housing 310 defining an internal chamber 320. The internal chamber 320 is in fluid communication with an inlet fluid pathway 312 and an outlet fluid pathway 314. The inlet fluid pathway 312 and the outlet fluid pathway 314 may be configured for fluid communication with associated fluid paths 210A, 210B of the fluid injector system 2000. The at least one air bubble suspension apparatus 300 may be connected to the associated fluid path 210A, 210B such that injection fluid injected from the associated syringe 10A, 10B flows into the inlet fluid pathway 312, through the interior chamber 320, and out of the outlet fluid pathway 314. The air bubble suspension apparatus 300 is located in each of the fluid paths 210A, 210B downstream of the at least one air detector 200 and upstream of the downstream shutoff valve 390 and, in some embodiments, upstream of the bulk fluid valves 215A, 215B. In this manner, the air bubble is at least temporarily suspended in the air bubble suspension apparatus 300 for a length of time to allow moving of the downstream shutoff valve 390 and/or the bulk fluid valves 215A, 215B to the closed position and stopping the injection procedure. In some embodiments, the air bubble suspension apparatus 300 may be configured to delay passage of the one or more air bubbles from the inlet fluid pathway 312 to the outlet fluid pathway 314 by at least 100 milliseconds.

The inlet fluid pathway 312 may be oriented relative to the internal chamber 320 such that fluid flow into the internal chamber 320 creates an internal fluid vortex in the injection fluid entering the internal chamber 320. In some embodiments, the inlet fluid pathway 312 may be oriented such that injection fluid from the inlet fluid pathway 312 enters the internal chamber 320 substantially tangent to a curved or hemispherical interior wall 322 of the internal chamber 320, thereby inducing the injection fluid to flow along the interior wall 322 to generate the fluid vortex. The internal fluid vortex induces one or more air bubbles that may be present in the injection fluid to be temporarily retained in the fluid vortex in the internal chamber 320, thereby at least temporarily delaying passage of the one or more air bubbles to the outlet fluid pathway 314 and out of the air bubble suspension apparatus 300. The internal fluid vortex may define a generally circular or otherwise continuous flow path along the curved or hemispherical interior wall 322 of the internal chamber 320 which causes the one or more air bubbles to be temporarily suspended in the injection fluid in the fluid vortex. In addition, the fluid vortex may induce the one or more air bubbles to coalesce into a smaller number of larger air bubbles, for example by collision and coalescence of small air bubbles. The curved or hemispherical interior wall 322 may minimize shear forces on the one or more air bubbles and thus, prevent the air bubble from shearing into smaller air bubbles in the vortex.

In various embodiments, the internal chamber 320 may have a volume (i.e. a fluid capacity) sufficient to delay a bubble of up to 0.5 milliliters (mL). In such embodiments, the internal chamber 320 may have a volume (i.e. a fluid capacity) of between 2 mL and 10 mL, in some embodiments between 2.8 mL to 3.6 mL, in some embodiments approximately 3.2 mL, and in some embodiments approximately 5.4 mL. In the embodiment shown in FIGS. 3-6, the internal chamber 320 may have a volume (i.e. a fluid capacity) of approximately 6.77 mL for delaying a bubble of up to approximately 0.5 mL. In the embodiment shown in FIGS. 7-8, the internal chamber 320 may have a volume (i.e. a fluid capacity) of approximately 7.00 mL for delaying a bubble of up to approximately 0.5 mL. In some embodiments, the volume of the internal chamber 320 may be increased accordingly in order to delay bubbles having a greater volume than 0.5 mL.

With continued reference to the various embodiments shown in FIGS. 3-25, the outlet fluid pathway 314 may be oriented relative to the internal chamber 320 to prevent the one or more air bubbles suspended in the internal fluid vortex from readily flowing toward the outlet fluid pathway 314. For example, the outlet fluid pathway 314 may be oriented such that the fluid flow path defined by the fluid vortex is directed away from the outlet fluid pathway 314, or such that fluid flowing within the internal chamber 320 must change direction in order to enter the outlet fluid pathway 314 (see, e.g., FIG. 14). In some embodiments, the outlet fluid pathway 314 may extend substantially perpendicular from the interior wall 322 of the internal chamber 320 such that fluid flow in the fluid vortex passes transversely across an opening 315 of the outlet fluid pathway 314 (see, e.g., FIG. 4). The outlet fluid pathway 314 may be arranged such that, in an injection position of the air bubble suspension apparatus 300, the outlet fluid pathway 314 extends at least partially downward from the internal chamber 320. As air is buoyant relative to the injection fluid in the internal chamber 320, any air bubbles present in the internal chamber 320 are induced by its relative buoyancy to float or migrate towards the top of the internal chamber 320 away from the outlet fluid pathway 314. In addition, with such a configuration for the air bubble suspension apparatus 300, the air bubble suspension apparatus 300 may be moved (e.g., rotated) from the injection position to a priming position in which the outlet fluid pathway 314 extends at least partially upward from the internal chamber 320 (see, FIG. 5). In the priming position, during a priming process to remove air from the fluid line prior to initiation of a fluid injection procedure, the air bubbles present in the internal chamber 320 are induced to float toward the outlet fluid pathway 314 so that under the influence of the priming fluid flow the air bubbles can be purged through the outlet fluid pathway 314 from a distal end of the associated fluid path 210A, 210B.

Figure 3:
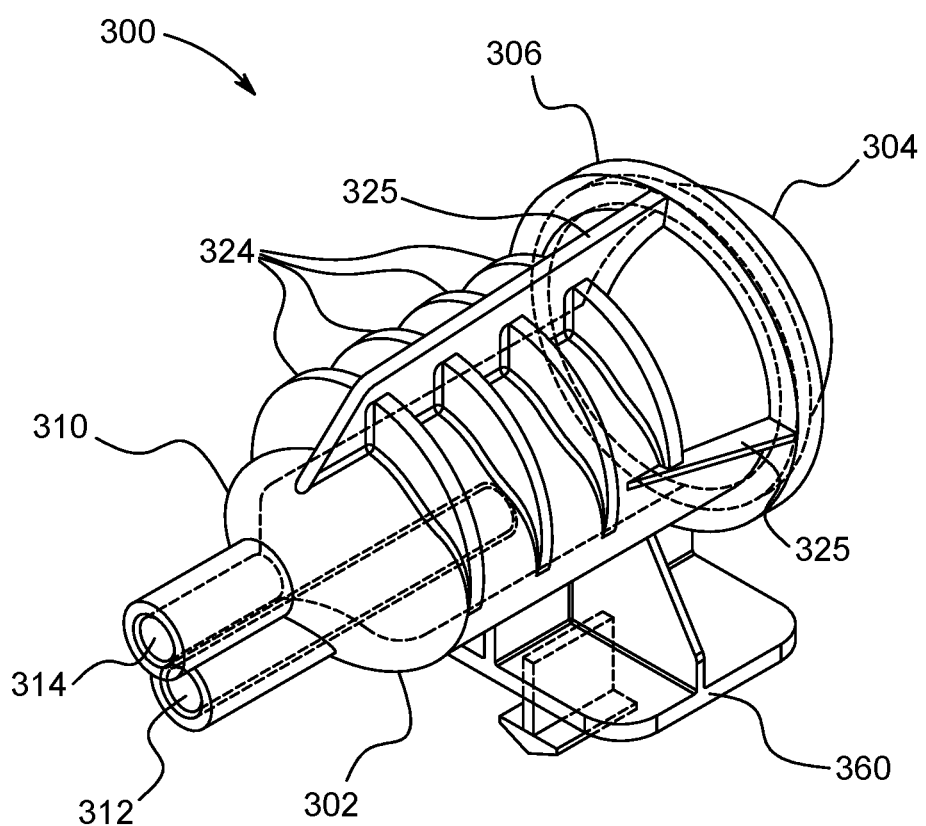
FIG. 3 is a perspective view of an air bubble suspension apparatus according to an embodiment of the present disclosure.
Figure 4:
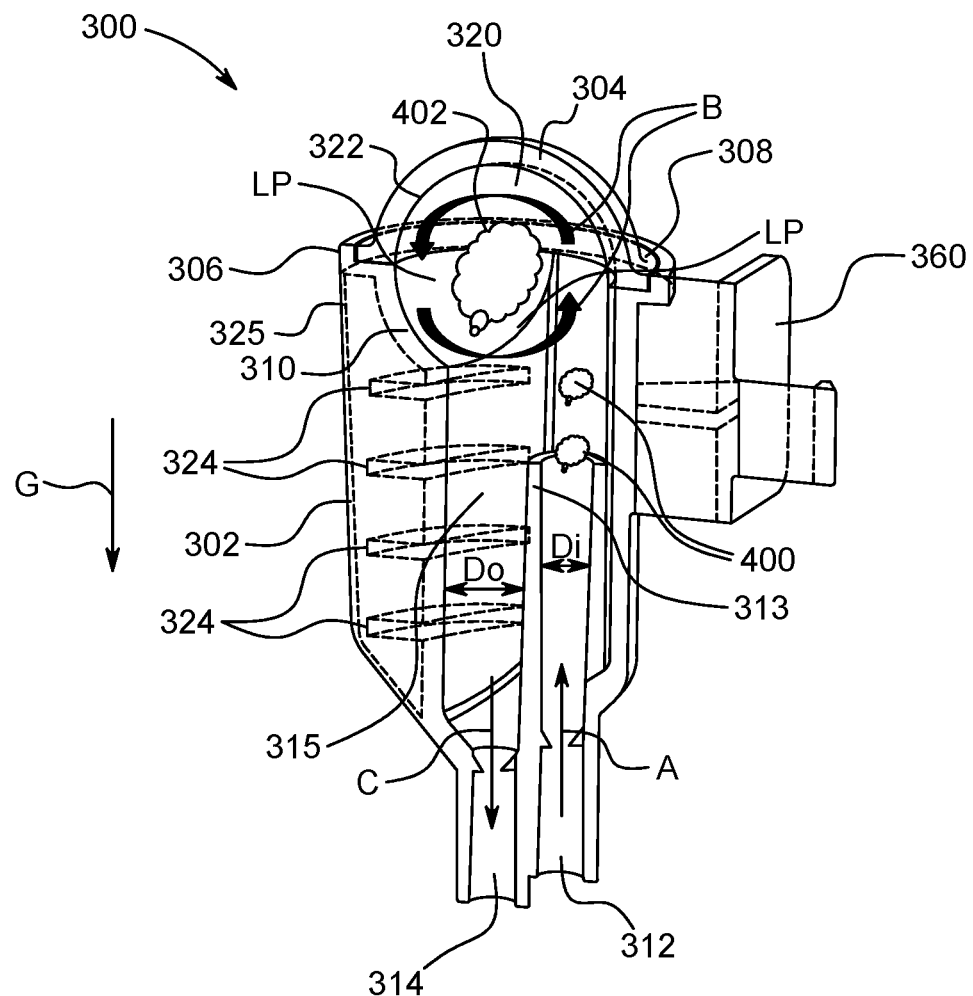
FIG. 4 is a cross-sectional side view of the air bubble suspension apparatus of FIG. 3 in an injection position.
Figure 5:
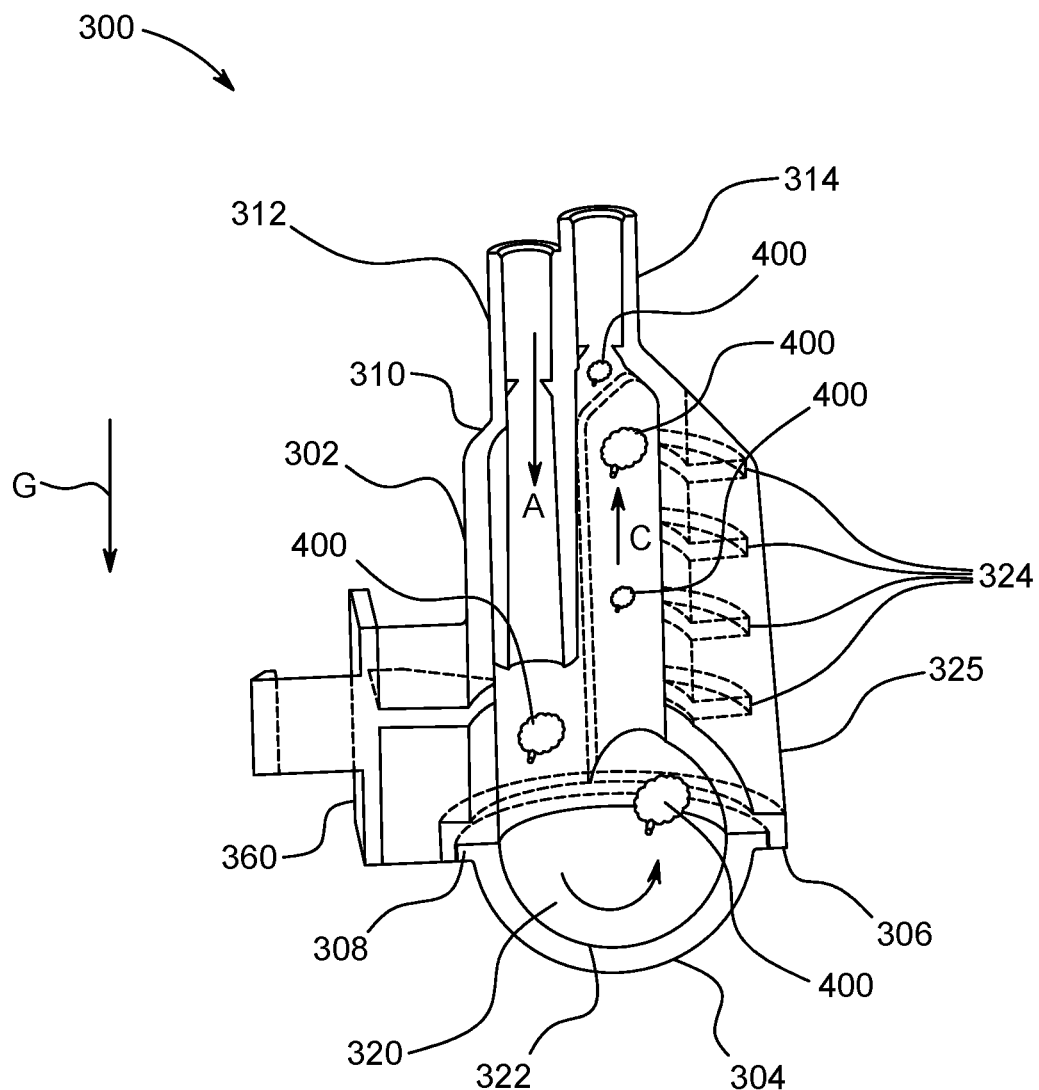
FIG. 5 is a cross-sectional side view of the air bubble suspension apparatus of FIG. 3 in a priming position.

With particular reference to FIGS. 3-5, an embodiment of the air bubble suspension apparatus 300 is shown. The housing 310 may be formed of a first housing section 302 and a second housing section 304. Forming the housing 310 from multiple sections may facilitate manufacture via an injection molding process to form the various features of the air bubble suspension apparatus 300. The air bubble suspension apparatus 300 may be made of any suitable medical grade material, such as a medical grade polymeric material that is capable of withstanding the high fluid pressures within the air bubble suspension apparatus 300. The first housing section 302 may include at least one of the inlet fluid pathway 312 and the outlet fluid pathway 314. In the embodiment shown in FIGS. 3-5, the first housing section 302 includes both the inlet fluid pathway 312 and the outlet fluid pathway 314. The inlet fluid pathway 312 and the outlet fluid pathway 314 may extend substantially parallel to one another. The internal chamber 320 may be defined by the first housing section 302 and the second housing section 304. In the embodiment shown in FIGS. 3-5, each of the first housing section 302 and the second housing section 304 partially define the internal chamber 320. As shown in FIGS. 4 and 5, the first housing section 302 includes a flange 306 configured to receive an end feature 308, for example a lip, of the second housing section 304. In some embodiments, the flange 306 may be provided on the second housing section 304 and the end feature 308 may be provided on the first housing section 302. The first housing section 302 and the second housing section 304 may be joined via an adhesive, laser welding, ultrasonic welding, or the like. The housing 310 may include one or more strengthening ribs 324, 325 located at various positions to provide support against the high fluid pressure within the housing 310. In some angiography (CV) procedures, fluid pressure may be up to approximately 1200 psi. In some embodiments, a plurality of strengthening ribs 324 may extend radially from at least a portion of the inlet fluid pathway 312, the first housing section 302, the second housing section 304, and the outlet fluid pathway 314. In some embodiments, at least one strengthening rib 325 may extend parallel with the inlet fluid pathway 312 and/or the outlet fluid pathway 314. In certain embodiments, connector arm 360 may additionally act as a strengthening feature for inlet fluid pathway 314.

With continued reference to FIGS. 3-5, the internal chamber 320 may have a curved, hemispherical interior wall 322 to induce the injection fluid entering in the internal chamber 320 to flow in the internal fluid vortex, identified in FIG. 4 by vortex flow path B. In some embodiments, the interior wall 322 of the internal chamber 320 defined by the second housing section 304 may be substantially hemispherical or domed. As shown in FIG. 4, which illustrates the air bubble suspension apparatus 300 is shown in the injection position, the fluid inlet pathway 312 may extend into the internal chamber 320 substantially tangent to the interior wall 322 to create the internal fluid vortex. The fluid inlet pathway 312 may have an opening 313 into the internal chamber 320 such that injection fluid flowing into the internal chamber 320 in the direction A merges with the injection fluid in the internal chamber 320 flowing in the fluid vortex flow path B. The injection fluid flowing into the internal chamber 320 from the fluid inlet pathway 312 thus enters the internal fluid vortex in substantially the same direction as the vortex flow path B to sustain the fluid vortex. The fluid vortex flow path B thus flows continuously within the internal chamber 320 so long as injection fluid continues to be introduced into the internal chamber 320 from the fluid inlet pathway 312. The interior wall 322 may be shaped to induce recirculation of the injection fluid into the vortex flow path B.

With continued reference to FIG. 4, the outlet fluid pathway 314 may extend from the internal chamber 320 substantially perpendicular to the interior wall 322 and the fluid vortex flow path B, such that the fluid vortex flow path B flows transversely across an opening 315 of the outlet fluid pathway 314. As such, at least some of the injection fluid in the fluid vortex flow path B flows past the opening 315 and back toward the opening 313 of the fluid inlet pathway 312 to sustain the fluid vortex.

With continued reference to FIG. 4, the internal fluid vortex may suspend one or more air bubbles 400 in the internal chamber 320 during an injection procedure executed by the fluid injector system 2000. As injection fluid is introduced into the internal chamber 320 via the inlet fluid pathway 312, any air bubbles 400 present in the incoming injection fluid migrate toward a low pressure region LP formed by the internal fluid vortex at a center of the fluid vortex flow path B. The injection fluid flowing in the fluid vortex flow path B form a boundary that at least temporarily suspends the one or more air bubbles 400 within the low pressure region and at least temporarily delays passage of the one or more air bubbles 400 toward the outlet fluid pathway 314. The one or more air bubbles 400 suspended in the low pressure region LP may coalesce to form one or more larger air bubbles 402. The interior wall 322 may be shaped to induce recirculation of the injection fluid into the vortex flow path B, and to induce the one or more air bubbles 400 into a tighter formation within the vortex flow path B. Even so, during the course of the injection the one or more larger air bubbles 402 may be sheared or shredded by fluid forces into smaller bubbles 404 that can migrate outside of vortex flow path B.

With continued reference to FIG. 4, in the injection position, the housing 310 is oriented such that the outlet fluid pathway 314 extends substantially vertically downward from the internal chamber 320. As such, a flow direction C of injection fluid flowing out of the internal chamber 320 is substantially aligned with a direction of gravity G. As air is buoyant relative to the injection fluid, buoyancy of air bubbles 400, 402 in the internal chamber 320 induces the one or more air bubbles 400, 402 to tend to rise opposite the direction of gravity G toward an upper region of the internal chamber 320, and therefore the air bubbles 400, 402 tend to remain suspended in the internal fluid vortex in the internal chamber 320 for a longer period of time. Further, even the sheared air bubbles 404 which cross the boundary formed by the fluid vortex flow path B are induced by buoyancy to tend to flow opposite the direction of gravity G and thus are further delayed from moving through the outlet fluid pathway 314.

In some embodiments, at least a portion of the outlet fluid pathway 314 may have a cross-sectional diameter Do greater than a cross-sectional diameter Di of the inlet fluid pathway 312. The greater diameter Do of the outlet fluid pathway 314 may reduce flow velocity at the outlet fluid pathway 314 of fluid exiting the internal chamber 320. The reduced flow velocity consequently reduces the drag forces on the bubbles 404 outside the boundary formed by the fluid vortex flow path B, such that the buoyancy of the bubbles 404 may tend to overcome the drag forces inducing the bubbles 404 toward the outlet fluid pathway 314. As a result, the bubbles 404 may be at least temporarily delayed from flowing out of outlet fluid pathway 314.

With continued reference to FIG. 4, in some embodiments, the diameter Di of the inlet fluid pathway 312 may be selected to control the flow velocity of the injection fluid, including air bubbles 400 contained therein, into the internal chamber 320. In particular, reducing the diameter Di increases the flow velocity. The diameter Di of the inlet fluid pathway 312 may be selected to produce a relatively high flow velocity, which has the effect of shredding the one or more air bubbles 400. In some embodiments, the diameter Di of the inlet fluid pathway 312 may be approximately 3.7 mm (0.145 inches).

Referring again to FIG. 5, the air bubble suspension apparatus 300 is shown in the priming position for performing a priming or purging operation in which fluid is injected to prime/purge the air bubble suspension apparatus 300 and the associated fluid paths 210A, 210B prior to an injection procedure to remove any air from the air bubble suspension apparatus 300 and the associated fluid paths 210A, 210B. In the priming position, the housing 310 is oriented such that the inlet fluid pathway 312 and the outlet fluid pathway 314 extend substantially vertically upward from the internal chamber 320. As such, the flow direction A of injection fluid flowing into the internal chamber 320 through inlet fluid pathway 312 is substantially in line with the direction of gravity G. The diameter Di of the inlet fluid pathway 312 may be sufficiently small that fluid flow velocity in the inlet fluid pathway 312 can carry the air bubbles 400 against the direction of buoyancy of the air bubbles 400. That is, the flow velocity through the diameter Di generates sufficient drag force on the one or more bubbles 400 to overcome the force of the buoyant nature of the air bubbles 400 and drags the air bubbles 400 into the internal chamber 329. As a result, the one or more bubbles 400 are transported by the injection fluid into the internal chamber 320.

In the priming position, the outlet fluid pathway 314 also extends substantially vertically upward from the internal chamber 320, such that the flow direction C of injection fluid flowing out of the internal chamber 320 is substantially opposite the direction of gravity G. Buoyancy of the air bubbles 400 in the internal chamber 320 induces the air bubbles 400, 402 to float upward from the internal fluid vortex through the outlet fluid pathway 314, working in concert with the drag associated with the fluid flow and thereby purging the air bubble suspension apparatus 300 of air bubbles 400.

With continued reference to FIGS. 3-5 the air bubble suspension apparatus 300 may include a connector arm 360 extending from the housing 300. The connector arm 360 may be configured for connection to the injector housing 12 or other feature associated with the flow path or injector (see FIGS. 1-2). In particular, the connector arm 360 may be configured to interface with an actuator in communication with the controller 900 (see FIG. 2) of the fluid injector system 2000. The controller 900 may be programmed or configured to rotate the air bubble suspension apparatus 300 between the injection position and the priming position via the connector arm 360 according to an injection protocol. Alternatively, the connector arm 360 may be configured to attach to the fluid injector system in either the injection or priming position and may be configured for a user to manually rotate the air bubble suspension apparatus 300 between the injection position and the priming position via the connector arm 360, for example in response to a prompt by the system on a GUI, to prepare the fluid injector for a fluid injection procedure.

Figure 6:
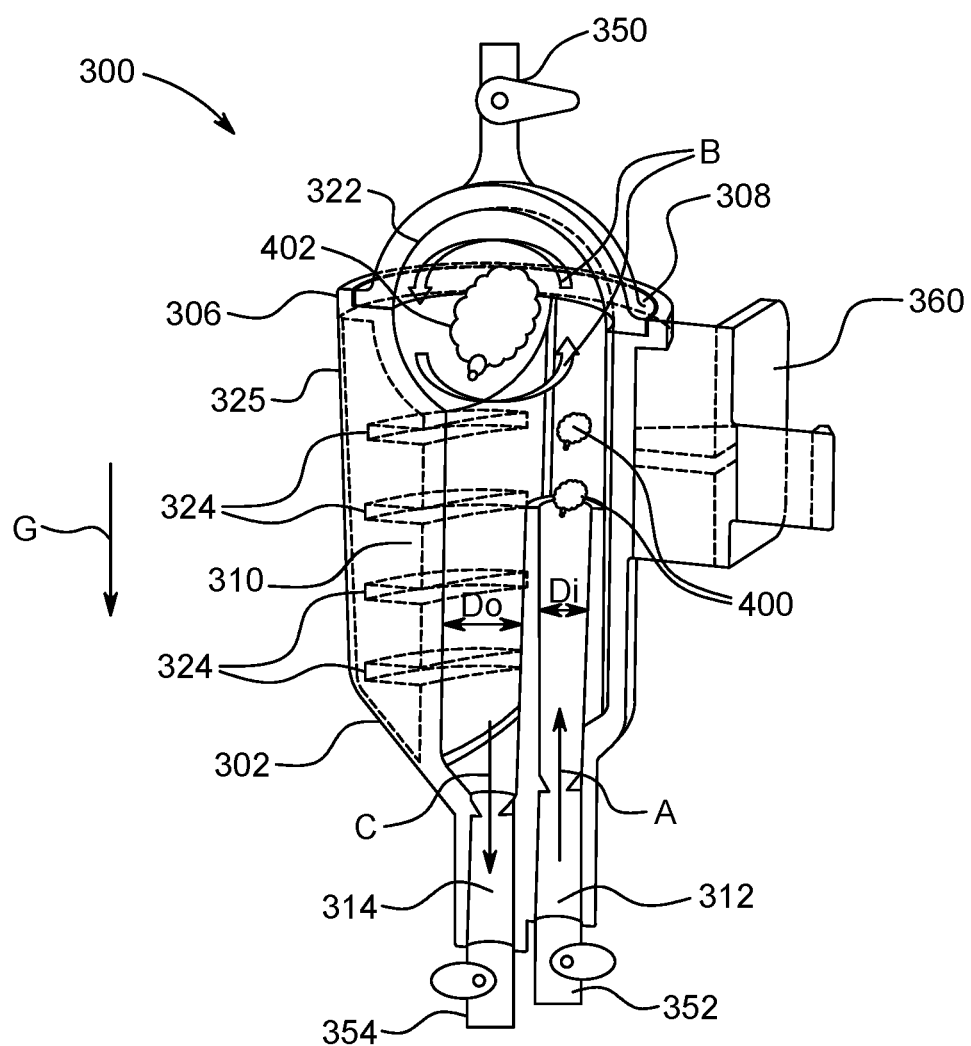
FIG. 6 is a cross-sectional side view of the air bubble suspension apparatus according to an embodiment of the present disclosure.

Referring now to FIG. 6, an embodiment of the air bubble suspension apparatus 300 is shown. The embodiment of the air bubble suspension apparatus shown in FIG. 6 may be substantially similar to the embodiment shown in FIGS. 3-5, and only the differences therebetween will be discussed below. The embodiment of the air bubble suspension apparatus 300 shown in FIG. 6 may include an air purging valve 350 on the housing 310 in fluid communication with the internal chamber 320. The air purging valve 350 may particularly be disposed in fluid communication with the uppermost region of the internal chamber 320. The air purging valve 350 may be used to drain air accumulated in the internal chamber 320, particularly after completion of an injection procedure when using a multi-patient setup for conducting multiple sequential injection sequences using a multi-patient disposable set and a single patient disposable set. The air purging valve 350 may be set to a closed position during performance of the injection procedure such that any air bubbles 400, 402 present in the injection fluid are suspended in the internal chamber 320 in the same manner described in connection with FIGS. 3-5. Upon completion of an injection procedure and before initiation of a subsequent injection procedure, the internal fluid vortex and the vortex flow path B (shown in FIG. 4) dissipate due to the absence of fluid flow into the internal chamber 320. As such, the vortex flow path B (shown in FIG. 4) no longer presents a flow boundary to the one or more coalesced air bubbles 402 suspended in the internal chamber 320. The one or more coalesced air bubbles 402 may thus buoyantly float to the uppermost region of the internal chamber 320 adjacent the air purging valve 350. The air purging valve 350 may be moved to an open position, either manually by an operator or automatically by the controller 900 such that the one or more coalesced air bubbles 402 may flow out of the internal chamber 320 via the air purging valve 350, for example with a low fluid flow into the chamber to replace the volume of the purged air with fluid. In some embodiments, an outlet of the air purging valve 350 may be connected to a vacuum source, such as a hand syringe (not shown), to assist in removing the one or more coalesced air bubbles 402 from the internal chamber 320. After the one or more coalesced air bubbles 402 are removed from the internal chamber 320, the air purging valve 350 may be returned to the closed position in preparation for a subsequent injection procedure. Air purging valve 350 may be a stopcock, pinch valve, or the like.

With continued reference to FIG. 6, some embodiments the air bubble suspension apparatus 300 may include an adjustable valve 352 associated with the inlet fluid pathway 312 and/or an adjustable valve 354 associated with the outlet fluid pathway 314. The adjustable valve 352 may be configured to change a cross-sectional area of the inlet fluid pathway 312, and the adjustable valve 354 may be configured to change a cross-sectional area of the outlet fluid pathway 314. Reducing the cross-sectional area of the inlet fluid pathway 312 and/or the outlet fluid pathway 314 increases flow velocity, whereas increasing the cross-sectional area of the inlet fluid pathway 312 and/or the outlet fluid pathway 314 reduces flow velocity. In some embodiments, it may be desirable to increase the cross-sectional area of the inlet fluid pathway 312, thereby reducing flow velocity through the inlet fluid pathway 312, as the reduced flow velocity may be less likely to dislodge air bubbles adhered to surfaces of the inlet fluid pathway 312. In some embodiments, it may be desirable to increase the cross-sectional area of the outlet fluid pathway 314, thereby reducing flow velocity through the outlet fluid pathway 314, as the reduced flow velocity may be less likely to carry air bubbles from the fluid vortex 402 through the outlet fluid pathway 314. The adjustable valves 352, 354 may be stopcocks, pinch valves, or the like.

Figure 7:
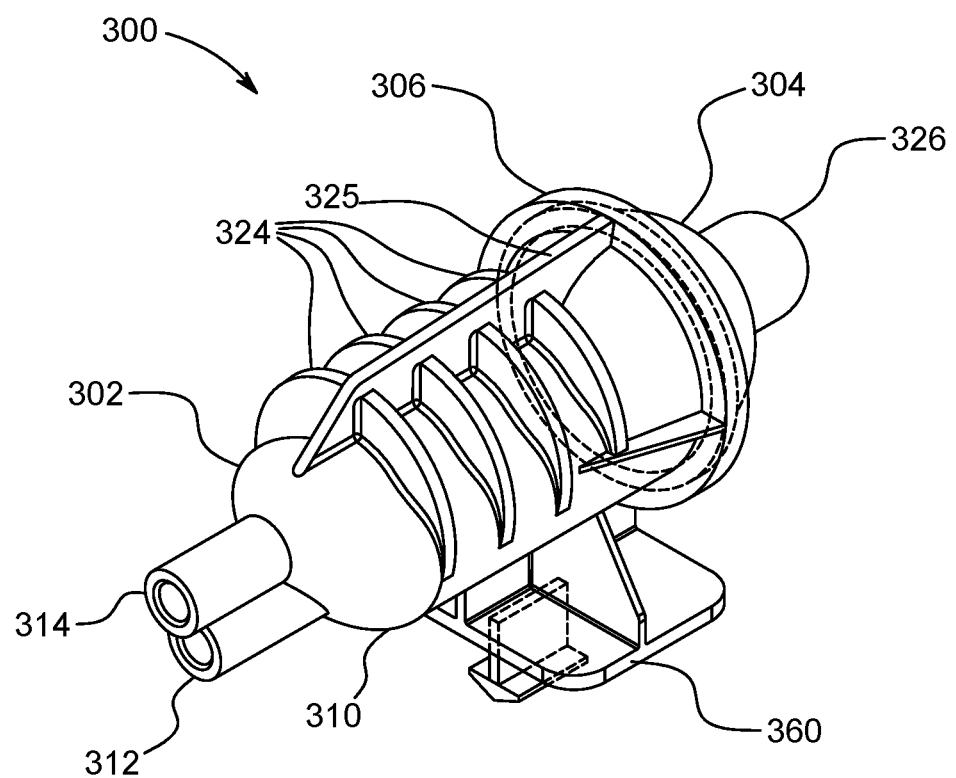
FIG. 7 is a perspective view of an air bubble suspension apparatus according to an embodiment of the present disclosure.
Figure 8:
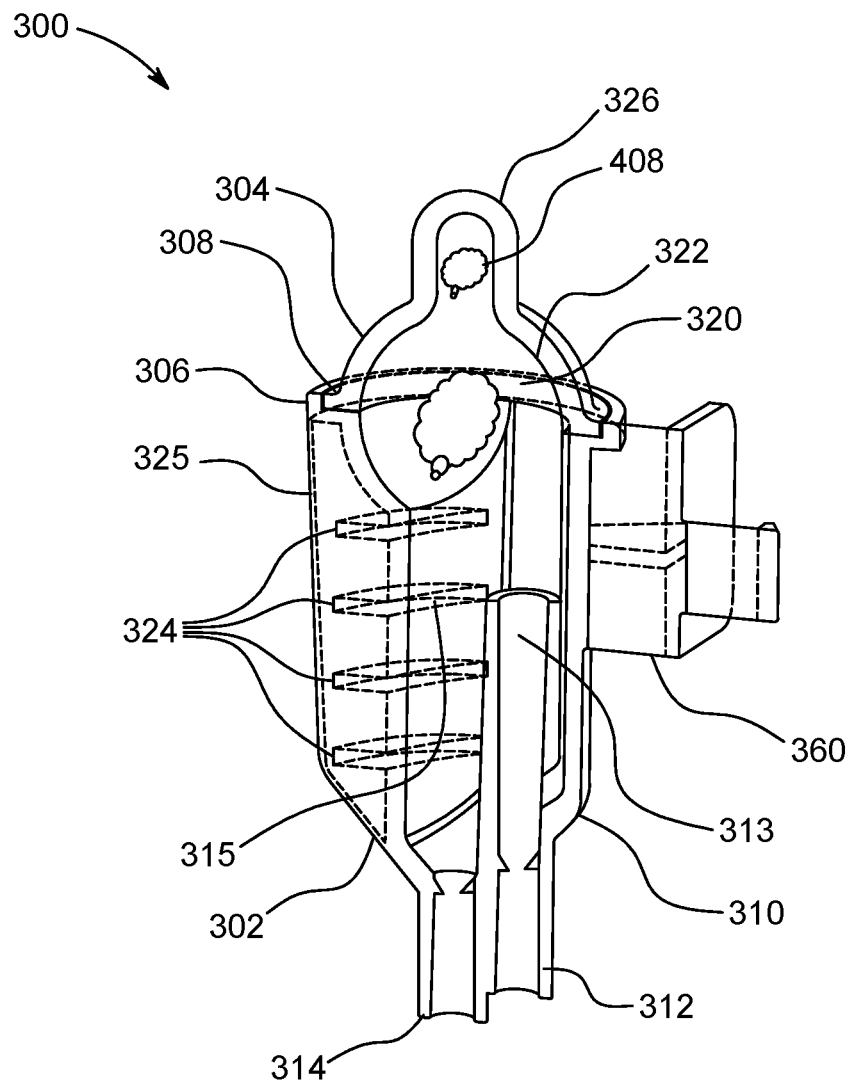
FIG. 8 is a cross-sectional side view of the air bubble suspension apparatus of FIG. 7 in an injection position.

Referring now to FIGS. 7-8, an embodiment of the air bubble suspension apparatus 300 is shown. The embodiment of the air bubble suspension apparatus 300 shown in FIGS. 7-8 may be substantially similar to the embodiments shown in FIGS. 3-6, and only the differences will be discussed below. The embodiment of the air bubble suspension apparatus 300 shown in FIGS. 7-8 may include a recess 326 defined in the interior wall 322 and extending radially outward from an upper most region of the internal chamber 320 substantially opposite the outlet fluid pathway 314. The recess 326 may receive and retain one or more air bubbles 408. The recess 326 may be particularly adapted to receive and retain one or more air bubbles 408 in the form of microbubbles generated by outgassing of a medical fluid. In some embodiments, an air purge valve 350 such as described in connection with FIG. 6 may be disposed on recess 326 such that the one or more air bubbles 408 accumulated in the recess 326 can be drained from the recess 326.

Referring now to FIGS. 9-14, an embodiment of the air bubble suspension apparatus 300 is shown. The embodiment of the air bubble suspension apparatus 300 shown in FIGS. 9-14 may include several common features and components with the embodiments shown in FIGS. 3-8, and any elements not specifically described in connection with FIGS. 9-14 are understood to be substantially similar to like elements of the embodiments of FIGS. 3-8. In the embodiment of the air bubble suspension apparatus 300 shown in FIGS. 9-14, the housing 310 includes a screen 328 dividing the internal chamber 320 into an inlet portion 332 and an outlet portion 334. Various embodiments of screen 328 are described herein in relation to FIGS. 19-24. The screen 328 may be disposed proximal to the outlet fluid pathway 314. The screen 328 may include at least one aperture 340 providing fluid communication between the inlet portion 332 and the outlet portion 334. Injection fluid flowing into the internal chamber 320 from the inlet fluid pathway 312 must subsequently flow through the at least one aperture 340 of the screen 328 to reach the outlet fluid pathway 314. In some embodiments, the screen 328 may include at least one funnel shaped aperture 342 defining the at least one aperture 340. The funnel 342 may taper from a maximum cross-sectional area adjacent the inlet portion 332 of the internal chamber 320 to a minimum diameter extending into the outlet portion 334 of the internal chamber 320. In some embodiments, at least a portion of the screen 328 may have a hydrophilic coating that induces air bubbles in the injection fluid to adhere to screen 328, and at least temporarily delaying the flow of such air bubbles toward outlet fluid pathway 314.

With continued reference to FIGS. 9-14, the air bubble suspension apparatus 300 may further include an extension tube 370 in fluid communication with and extending from the inlet fluid pathway 312 into the internal chamber 320. The extension tube 370 may include a tip 372 spaced apart from and past the flow axis of the outlet fluid pathway 314 such that the injection fluid flowing into the internal chamber 320 via the extension tube 370 is directed away from the outlet fluid pathway 314. In some embodiments, the extension tube 370 may extend past the at least one aperture 340 in the screen 328 causing injection fluid flowing into the internal chamber 320 from the inlet fluid pathway 312 to flow into the vortex flow path B prior to reaching the at least one aperture 340. The inlet portion 332 of the internal chamber 320 may be at least partially hemispherical or domed where the vortex flow path B flows along the interior wall 322 of the internal chamber 320.

With continued reference to FIGS. 9-14, the inlet fluid pathway 312 and the extension tube 370 may be oriented at an acute angle relative to the outlet fluid pathway 314 such that injection fluid entering the internal chamber 320 from the extension tube 370 is directed away from the opening 315 of the outlet fluid pathway 314.

Figure 10:
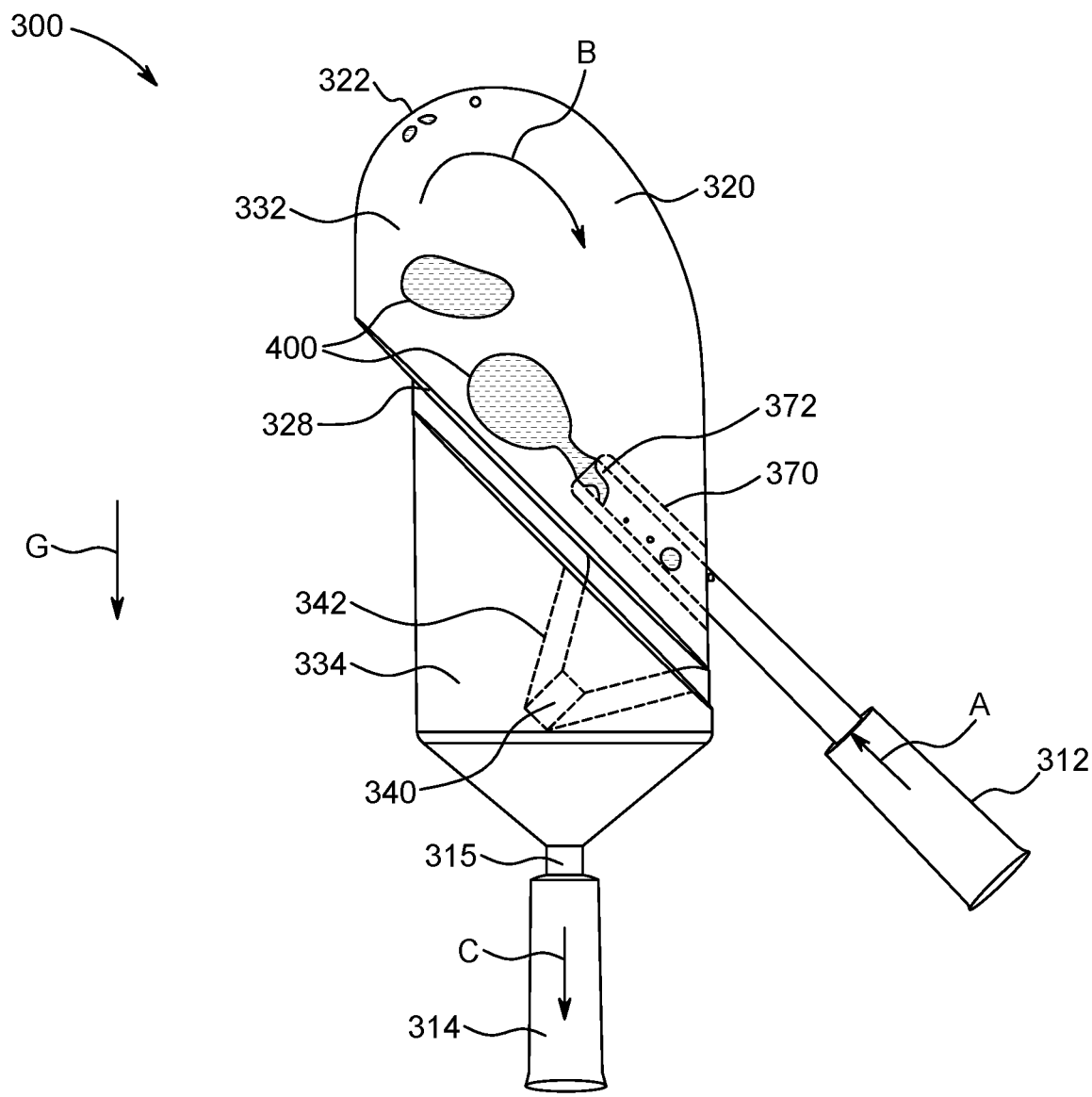
FIG. 10 is a cross-sectional side view of the air bubble suspension apparatus of FIG. 9 at a first time interval of an injection protocol.

With reference to FIGS. 10-13, a sequence showing an embodiment of a bubble suspension effect within the internal chamber 320 during performance of an injection procedure is shown. Referring first to FIG. 10, injection fluid may flow in the direction A through the inlet fluid pathway 312 and the extension tube 370 into the internal chamber 320. One or more air bubbles 400 may be transported with the injection fluid into the internal chamber 320. The orientation of the extension tube 370 directs the injection fluid and the one or more bubbles 400 into the vortex flow path B. In addition, the buoyancy of the one or more bubbles 400 relative to the injection fluid inhibits flow of the one or more air bubbles through the at least one aperture 340 in the screen 328 toward the outlet fluid pathway 314.

Figure 11:
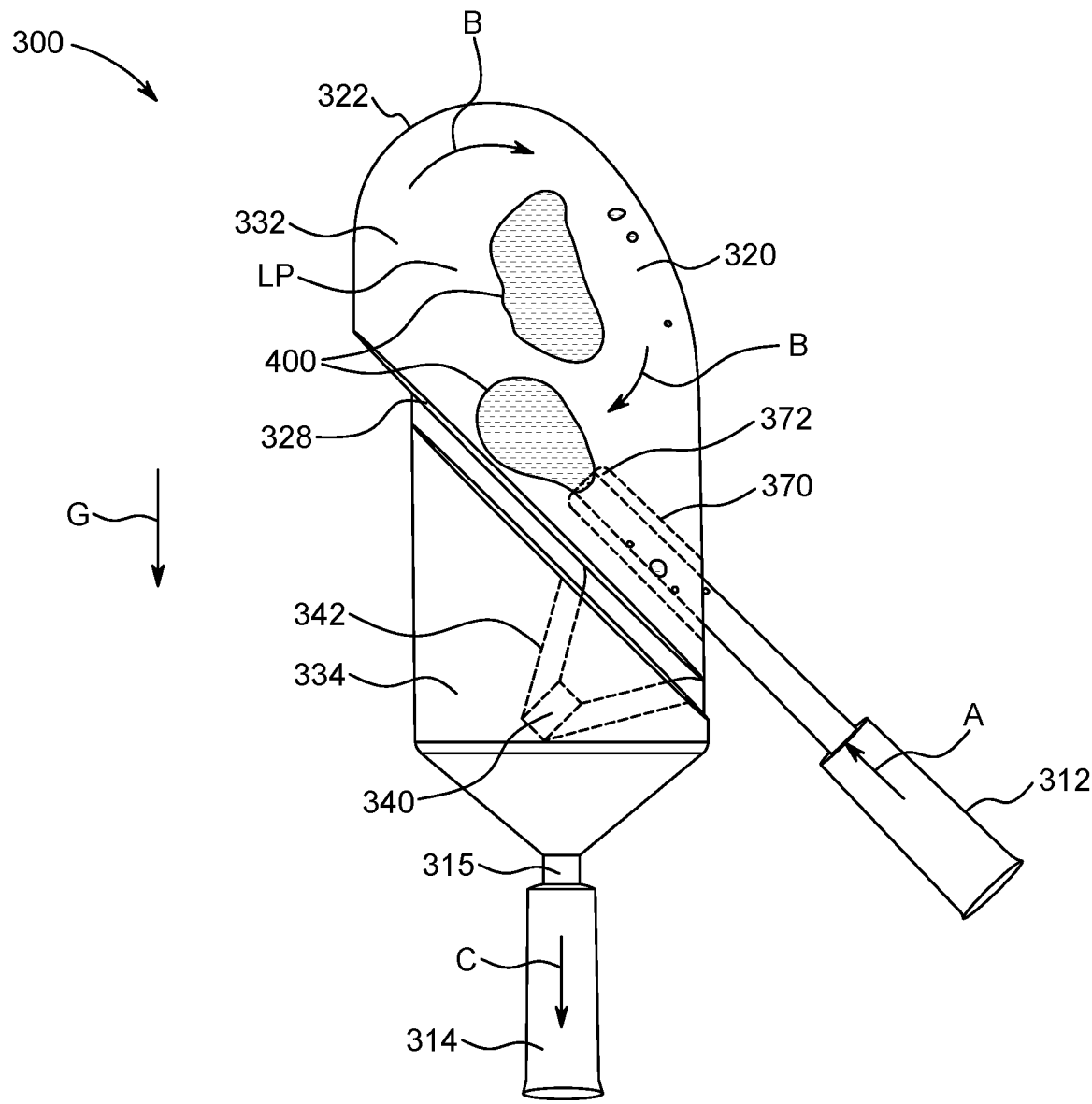
FIG. 11 is a cross-sectional side view of the air bubble suspension apparatus of FIG. 9 at a second time interval of an injection protocol.
Figure 12:
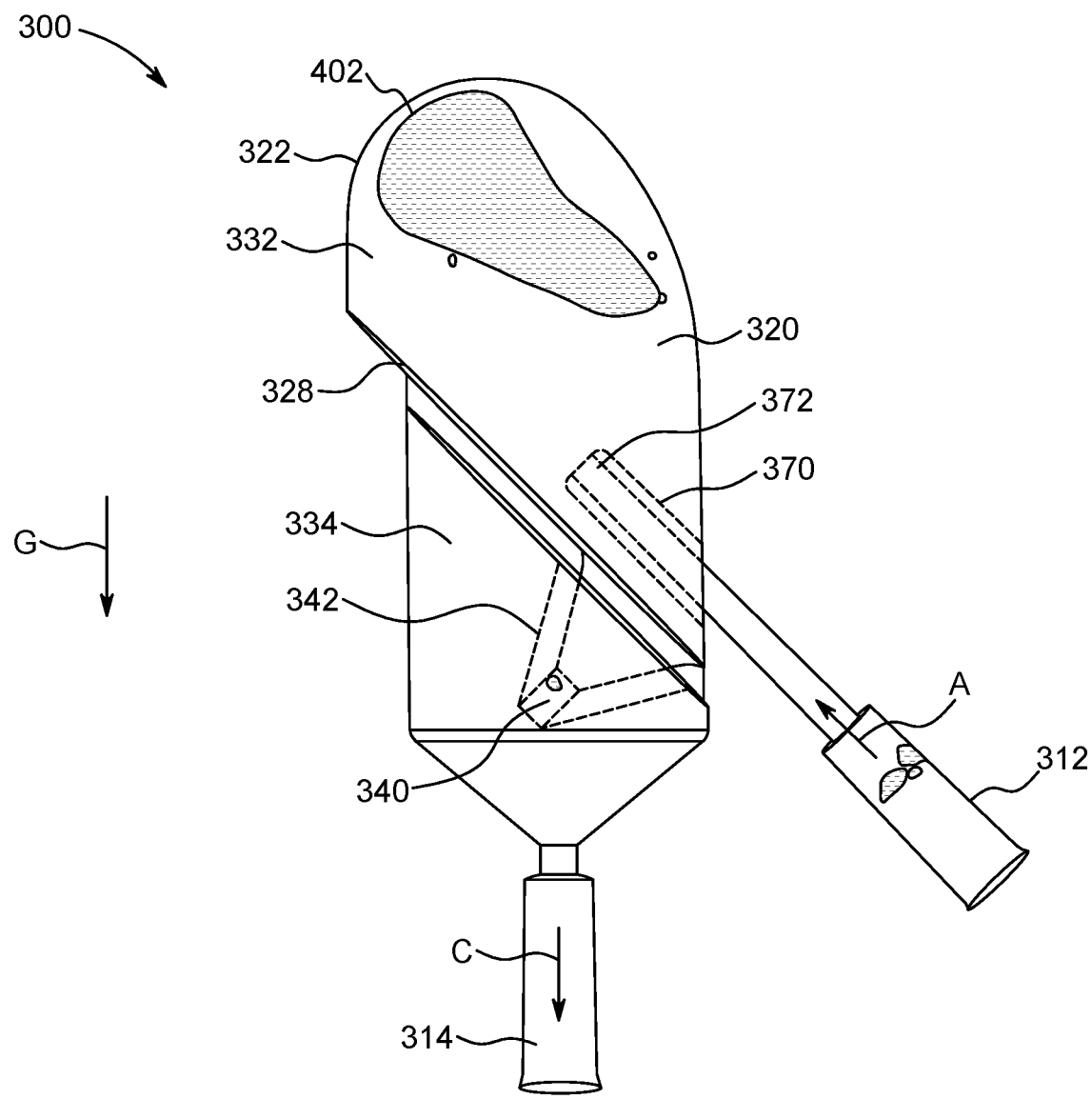
FIG. 12 is a cross-sectional side view of the air bubble suspension apparatus of FIG. 9 at a third time interval of an injection protocol.

Referring now to FIG. 11, as the injection fluid flows in the vortex flow path B, the one or more air bubbles 400 may migrate towards the low pressure region LP at the center of the vortex flow path B, thereby becoming at least temporarily suspended within the internal chamber 320. Further, the one or more air bubbles 400 may coalesce into one or more larger volume coalesced air bubbles 402 within the low pressure region LP, while injection fluid and additional air bubbles 400 continue to enter the internal chamber 320 via the extension tube 370 (see FIG. 12).

Figure 13:
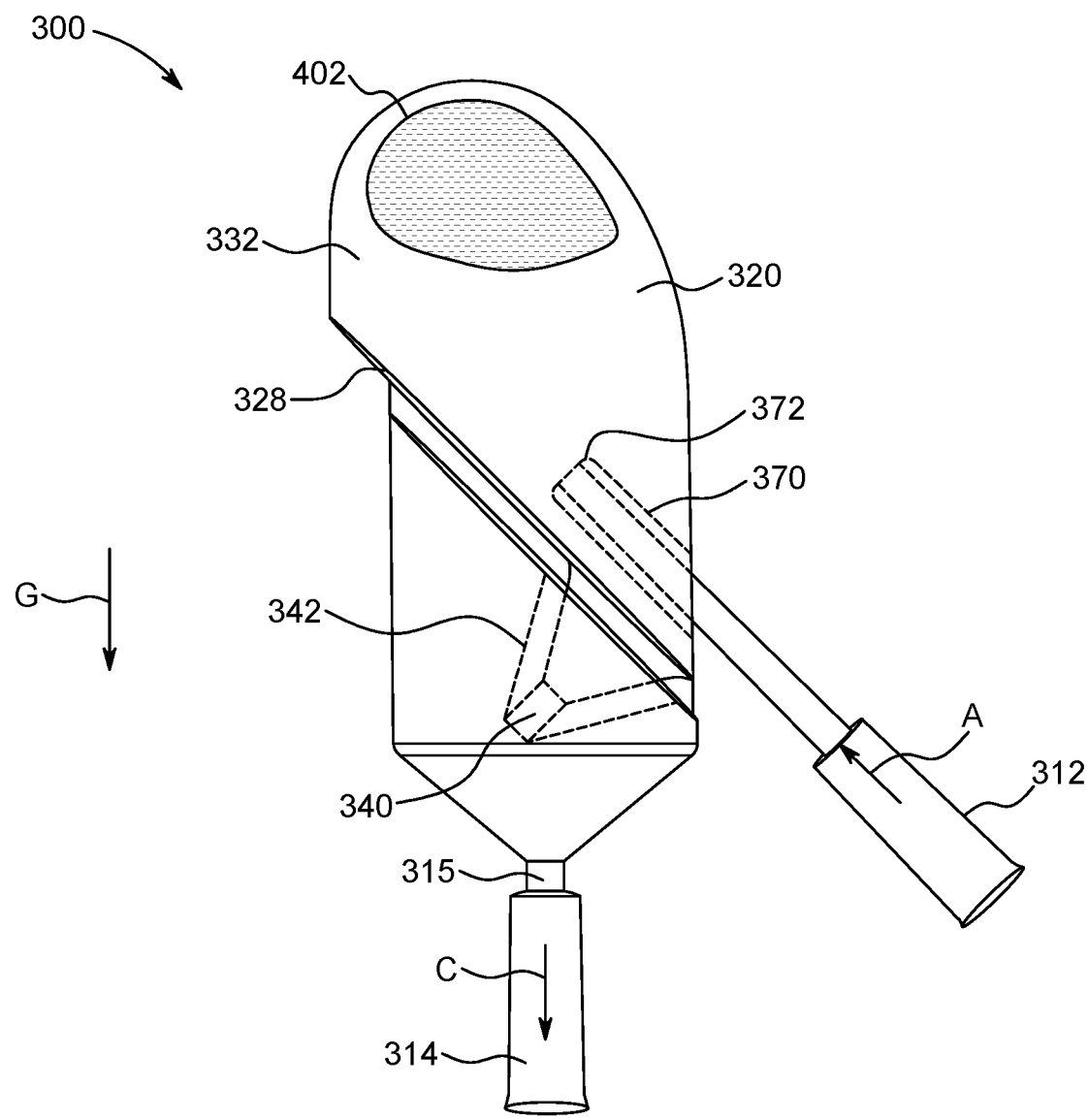
FIG. 13 is a cross-sectional side view of the air bubble suspension apparatus of FIG. 9 at a fourth time interval of an injection protocol.

FIG. 13 shows the air bubble suspension apparatus 300 after fluid flow into the internal chamber 320 has stopped, for example after completion of the injection procedure. With no new injection fluid being introduced into the internal chamber 320 to sustain the internal fluid vortex, the vortex flow path B (shown in FIGS. 9-12) dissipates and no longer presents a flow boundary to the one or more coalesced air bubbles 402 suspended in the internal chamber 320. The one or more coalesced air bubbles 402 may thus float to the uppermost region of the internal chamber 320 due to buoyancy of the one or more coalesced air bubbles 402 relative to the injection fluid. In some embodiments, the air bubble suspension apparatus 300 may include an air purging valve 350 (substantially as described herein in connection with FIG. 6) in fluid communication with the uppermost region of the internal chamber 320 to facilitate removal of the one or more coalesced air bubbles 402 from the internal chamber 320 for example between two injection procedures when a multi-patient injection sequence is used.

Figure 14:
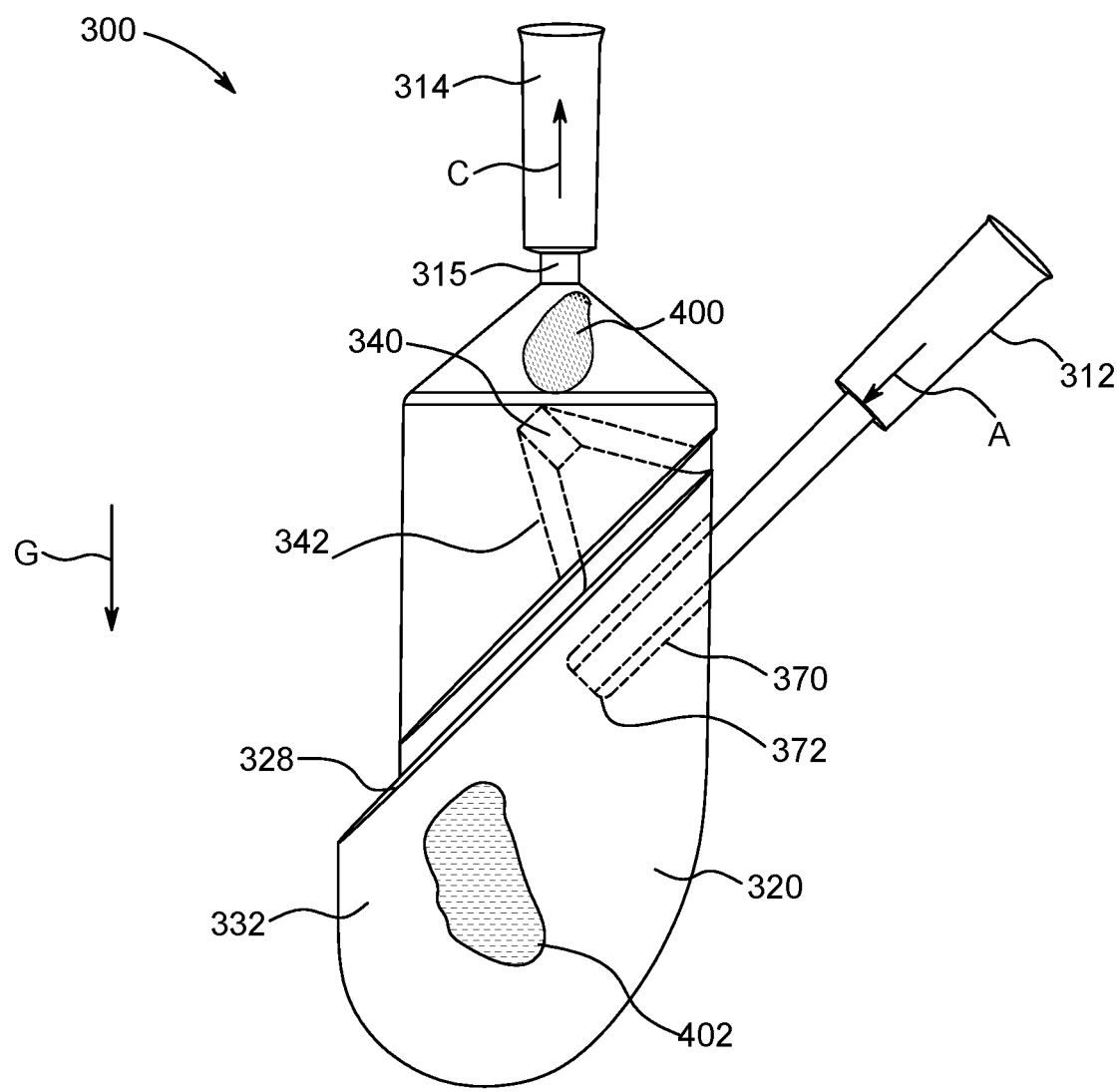
FIG. 14 is a cross-sectional side view of the air bubble suspension apparatus of FIG. 9 in a priming position.

With continued reference to FIGS. 9-14, the air bubble suspension apparatus 300 may be rotated approximately 180° from the injection position shown in FIGS. 10-13 to the priming position shown in FIG. 14. In the injection position, the outlet fluid pathway 314 extends substantially vertically downward from the internal chamber 320. As such, a flow direction C of injection fluid flowing out of the internal chamber 320 is substantially aligned with a direction of gravity G. As air is buoyant relative to the injection fluid, buoyancy of air bubbles 400, 402 in the internal chamber 320 induces the one or more air bubbles 400, 402 to tend to float opposite the direction of gravity G toward an upper region of the internal chamber 320, and therefore the air bubbles 400, 402 tend to remain suspended in the internal fluid vortex in the internal chamber 320. Further, even air bubbles which cross the boundary formed by the fluid vortex flow path B are induced to flow opposite the direction of gravity G and through the screen 328 and thus are further delayed from reaching the outlet fluid pathway 314.

In the priming position, shown in FIG. 14, the outlet fluid pathway 314 extends substantially vertically upward from the internal chamber 320 such that the flow direction C of injection fluid flowing out of the internal chamber 320 is substantially opposite the direction of gravity G. Buoyancy of air bubbles 400, 402 in the internal chamber 320 induces the air bubbles 400, 402 to flow from the chamber 320 through the outlet fluid pathway 314, thereby purging the air bubble suspension apparatus 300 of air.

Figure 9:
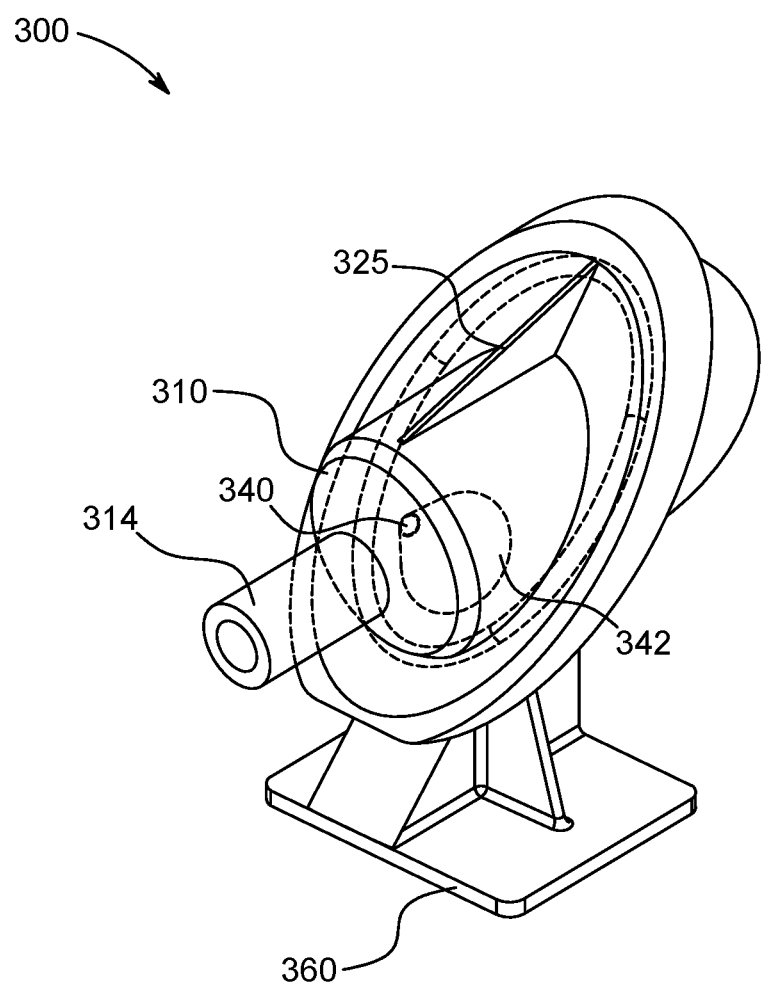
FIG. 9 is a perspective view of an air bubble suspension apparatus according to an embodiment of the present disclosure.

With reference to FIG. 9, the air bubble suspension apparatus 300 may include a connector arm 360 extending from the housing 300. The connector arm 360 may be configured for connection to the injector housing 12 or other feature associated with the flow path or injector system 2000 (see FIGS. 1-2). In particular, the connector arm 360 may be configured to interface with an actuator in communication with the controller 900 (see FIG. 2) of the fluid injector system 2000. The controller 900 may be programmed or configured to rotate the air bubble suspension apparatus 300 between the injection position and the priming position via the connector arm 360 according to an injection protocol. Alternatively, the connector arm 360 may be configured to attach to the fluid injector system in either the injection or priming position and may be configured for a user to manually rotate the air bubble suspension apparatus 300 between the injection position and the priming position via the connector arm 360, for example in response to a prompt by the system on a GUI 11, to prepare the fluid injector for a fluid injection procedure.

Figure 15:
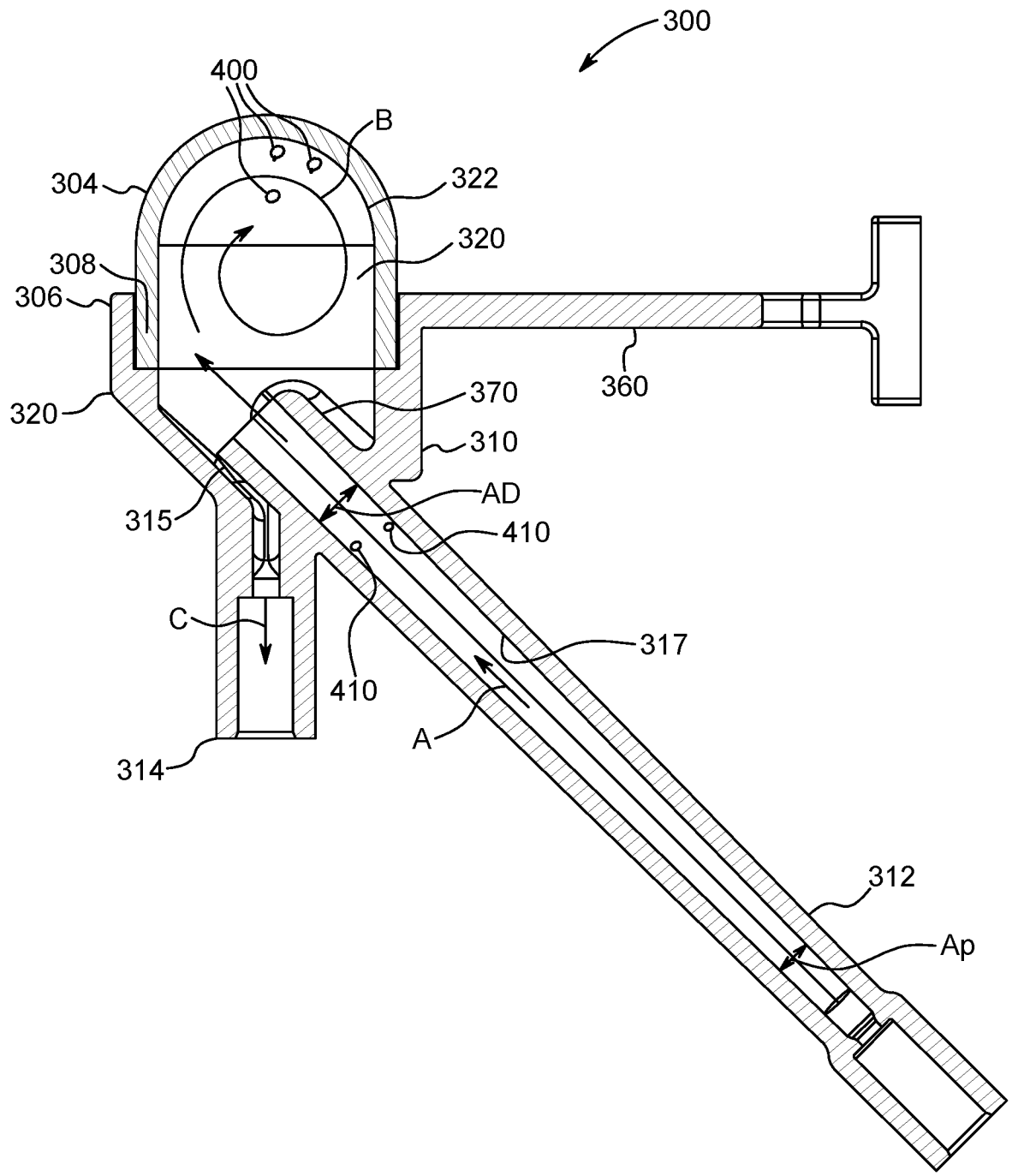
FIG. 15 is a cross-sectional side view of an air bubble suspension apparatus according to an embodiment of the present disclosure.
Figure 16:
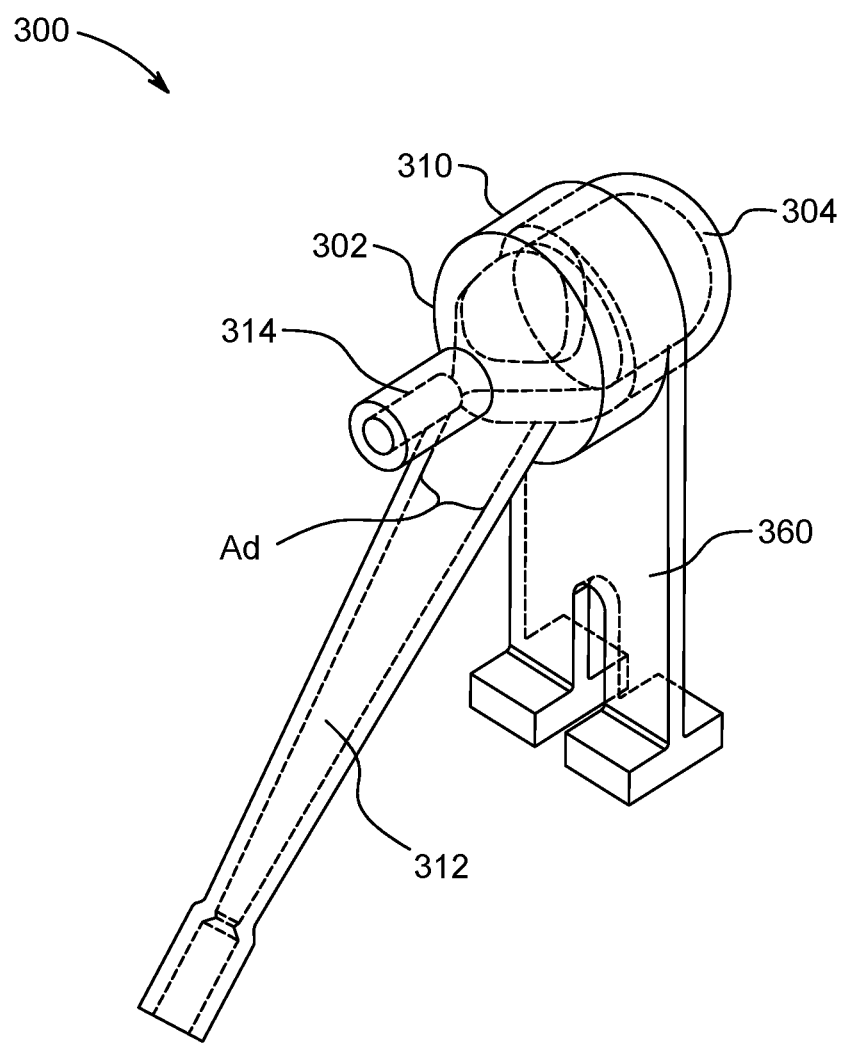
FIG. 16 is a perspective view of the air bubble suspension apparatus of FIG. 15.

Referring now to FIGS. 15 and 16, an embodiment of the air bubble suspension apparatus 300 is shown. The embodiment of the air bubble suspension apparatus 300 shown in FIGS. 15 and 16 may include many common features and components with various embodiments shown in FIGS. 3-13, and any elements not specifically described in connection with FIGS. 15 and 16 are understood to be substantially similar to like elements of any of the embodiments of FIGS. 3-13. In the embodiment of the air bubble suspension apparatus 300 shown in FIGS. 15 and 16, the housing 310 may be formed on the first housing section 302 and the second housing section 304, of which the first housing section 302 includes the inlet fluid pathway 312, extension tube 370, and the outlet fluid pathway 314. The inlet fluid pathway 312 may extend at an acute angle relative to the outlet fluid pathway 314. The second housing section 304 may be hemispherical or domed such that the vortex flow path B flows along the interior wall 322 of the internal chamber 320 in a circular or otherwise continuous manner. The first housing section 302 may include a flange 306 configured to receive an end feature 308, for example a lip, of the second housing section 304. In some embodiments, the flange 306 may be provided on the second housing section 304 and the end feature 308 may be provided on the first housing section 302. The first housing section 302 and the second housing section 304 may be joined via an adhesive, laser welding, ultrasonic welding, or the like.

With continued reference to FIGS. 15 and 16, the extension tube 370 may extend past the opening 315 of the outlet fluid pathway 314 such that injection fluid flowing into the internal chamber 320 is directed into the vortex flow path B away from the outlet fluid pathway 314. As with the embodiments shown in FIGS. 3-13, the vortex flow path B creates a boundary that at least temporarily delays passage of one or more air bubbles 400 suspended in the internal chamber 320 to the outlet fluid pathway 314. In some embodiments, the opening 315 of the outlet fluid pathway 314 may be positioned relative to the extension tube 370, for example underneath the extension tube 370, such that the extension tube 370 creates a flow obstruction to fluid and/or air bubbles 400 flowing toward the outlet fluid pathway 314.

In certain embodiments, the inner diameter of the inlet fluid pathway 312 may be tapered such that a proximal cross-sectional area Ap of the upstream inlet fluid pathway 312 is smaller than a distal cross-sectional area Ad of the downstream inlet fluid pathway 312. In some embodiments, the proximal cross-sectional area Ap may be substantially circular, and the distal cross-sectional area Ad may be substantially elliptical or oval. In some embodiments, by increasing the downstream cross-sectional area Ad relative to the upstream cross-sectional area Ap, the fluid flow velocity (for example between approximately 0.1 mL/second and 30 mL/second) in the inlet fluid pathway 312 may slow, allowing air bubbles 410 in the inlet fluid pathway 312 to adhere to a sidewall 317 of the larger cross-sectional area Ad, for example by surface tension. The reduced fluid flow velocity in the inlet fluid pathway 312 resulting from the enlarged distal cross-sectional area Ad may not be sufficient to immediately dislodge the adhered air bubbles 410 from the sidewall 317. That is, the adhesion force of the air bubbles 410 to the sidewall 317 may be greater than the force exerted on the air bubbles 410 by the injection fluid flowing through the distal cross-sectional area Ad. As such, the air bubbles 410 are at least temporarily delayed in flowing into the internal chamber 320 and thus delayed flowing out fluid outlet pathway 314. In some embodiments, the enlarged distal cross-sectional area Ad of the fluid inlet pathway 312 may allow injection fluid to flow around the air bubbles 410 adhered to the sidewall 317, rather than flowing into and potentially dislodging the air bubbles 410 adhered to the sidewall 317. In some embodiments, the enlarged distal cross-sectional area Ad of the fluid inlet pathway 312 may allow the air bubbles 410 to adhere to the sidewall 317 at least partially outside the primary flow path of the injection fluid through the fluid inlet pathway 312. In some embodiments, the inner surface of fluid inlet pathway 312 may be configured to attract and adhere air bubbles, such as by a surface treatment applied to the sidewall 317. Such features regarding different cross-sectional areas of the fluid inlet pathway 312 are also applicable to other embodiments of the air bubble suspension apparatus 300 described herein.

With continued reference to FIGS. 15 and 16, the air bubble suspension apparatus 300 may be rotated approximately 180° from the injection position shown in FIG. 15 to the priming position, analogous to FIG. 5 or 14. In the injection position, the outlet fluid pathway 314 extends substantially vertically downward from the internal chamber 320. As such, a flow direction C of injection fluid flowing out of the internal chamber 320 is substantially aligned with a direction of gravity G. As air is buoyant relative to the injection fluid, buoyancy of air bubbles 400, 402 in the internal chamber 320 induces the one or more air bubbles 400, 402 to tend to float opposite the direction of gravity G toward an upper region of the internal chamber 320, and therefore the air bubbles 400, 402 remain suspended in the internal fluid vortex in the internal chamber 320. Further, even air bubbles which cross the boundary formed by the fluid vortex flow path B are induced to flow opposite the direction of gravity G and through the screen 328 and thus are further delayed from reaching the outlet fluid pathway 314.

In the priming position, the outlet fluid pathway 314 extends substantially vertically upward from the internal chamber 320 such that the flow direction C of injection fluid flowing out of the internal chamber 320 is substantially opposite the direction of gravity G. Buoyancy of air bubbles 400, 402 in the internal chamber 320 induces the air bubbles 400, 402 to flow from the chamber 320 through the outlet fluid pathway 314, thereby purging the air bubble suspension apparatus 300 of air.

With continued reference to FIGS. 15 and 16, the air bubble suspension apparatus 300 may include a connector arm 360 extending from the housing 300. The connector arm 360 may be configured for connection to the injector housing 12 or other feature associated with the flow path or injector system 2000 (see FIGS. 1-2). In particular, the connector arm 360 may be configured to interface with an actuator in communication with the controller 900 (see FIG. 2) of the fluid injector system 2000. The controller 900 may be programmed or configured to rotate the air bubble suspension apparatus 300 between the injection position and the priming position via the connector arm 360 according to an injection protocol. Alternatively, the connector arm 360 may be configured to attach to the fluid injector system in either the injection or priming position and may be configured for a user to manually rotate the air bubble suspension apparatus 300 between the injection position and the priming position via the connector arm 360, for example in response to a prompt by the system on a GUI 11, to prepare the fluid injector for a fluid injection procedure.

Figure 17:
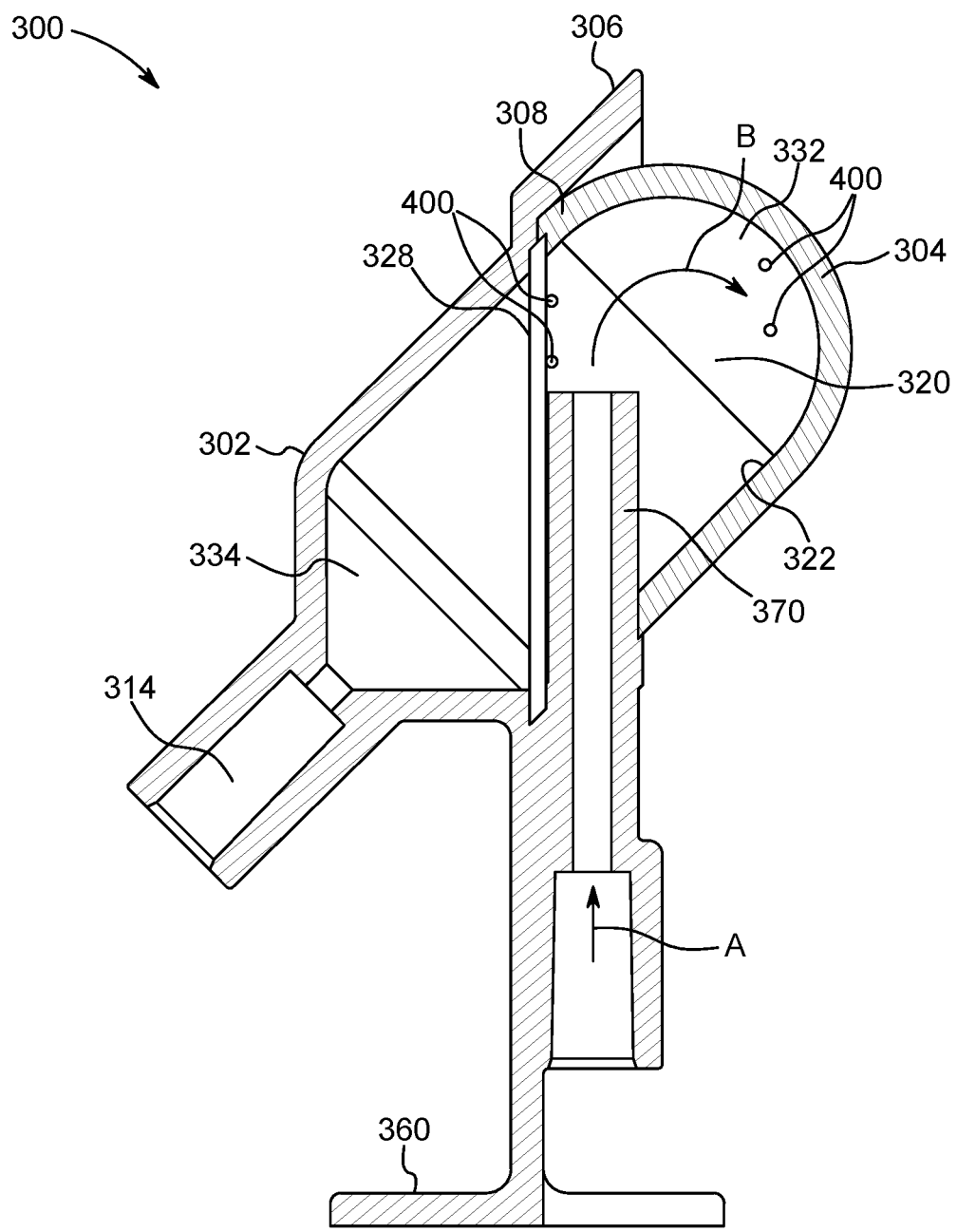
FIG. 17 is a cross-sectional side view of an air bubble suspension apparatus according to an embodiment of the present disclosure.
Figure 18:
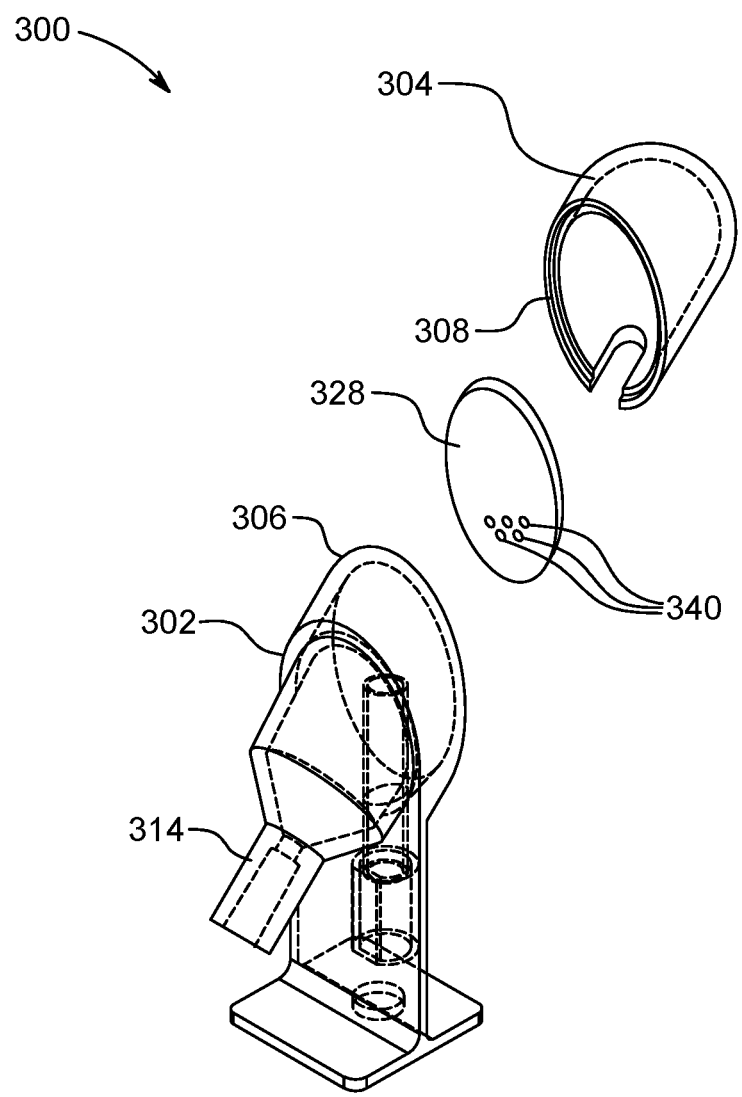
FIG. 18 is an exploded perspective view of the air bubble suspension apparatus of FIG. 17.

Referring now to FIGS. 17-18, an embodiment of the air bubble suspension apparatus 300 is shown. The embodiment of the air bubble suspension apparatus 300 shown in FIGS. 17-18 may include many common features and components with various embodiments shown in FIGS. 3-16 and particularly FIGS. 9-14, and any elements not specifically described in connection with FIGS. 17-18 are understood to be substantially similar to like elements of any of the embodiments of FIGS. 3-16. In the embodiment of the air bubble suspension apparatus 300 shown in FIGS. 17-18, the housing 310 may be formed by a first housing section 302 and a second housing section 304, of which the first housing section 302 includes the inlet fluid pathway 312, extension tube 370, and the outlet fluid pathway 314. The inlet fluid pathway 312 may extend at an acute angle relative to the outlet fluid pathway 314. The second housing section 304 may be hemispherical or domed such that the fluid vortex flow path B flows along the interior wall 322 of the internal chamber 320 in a circular or otherwise continuous manner. The first housing section 302 may include a flange 306 configured to receive an end feature 308, for example a lip, of the second housing section 304. In some embodiments, the flange 306 may be provided on the second housing section 304 and the end feature 308 may be provided on the first housing section 302. The first housing section 302 and the second housing section 304 may be joined via an adhesive, laser welding, ultrasonic welding, or the like.

With continued reference to FIGS. 17-18, a screen 328 may be provided between the first housing section 302 and the second housing section 304. In some embodiments, the screen 328 may be received within the flange 306 such that the end feature 308 retains the screen 328 in position between the first housing section 302 and the second housing section 304. The screen 328 may divide the internal chamber 320 into an inlet portion 332 and an outlet portion 334. The screen 328 may include at least one aperture 340 (as shown in FIGS. 19-24) providing fluid communication between the inlet portion 332 and the outlet portion 334.

Injection fluid flowing into the internal chamber 320 from the inlet fluid pathway 312 must subsequently flow through the at least one aperture 340 of the screen 328 to reach the outlet portion 334 and outlet fluid pathway 314. In some embodiments, the screen 328 may have a hydrophilic coating that induces air bubbles 400 in the injection fluid to adhere to the screen 328, for example, by increasing surface tension or adhesion therebetween, and thereby at least temporarily further delaying the flow of such adhered air bubbles 400 toward the outlet fluid pathway 314. The extension tube 370 may be positioned within the internal chamber 320 such that injection fluid entering the internal chamber is directed toward the vortex flow path B and away from the one or more apertures 340 of the screen 328. For example, the one or more apertures 340 of screen 328 may be located on a portion of screen 328 proximal to the distal outlet of extension tube 370.

Figure 19:
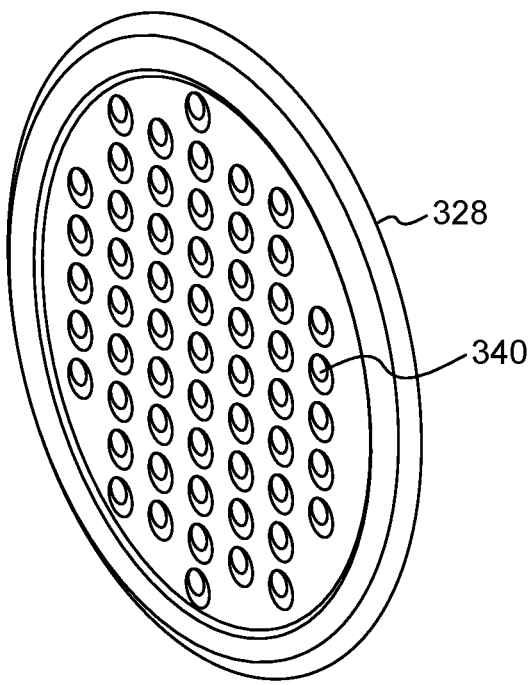
FIG. 19 is a perspective view of a screen for an air bubble suspension apparatus according to an embodiment of the present disclosure.
Figure 20:
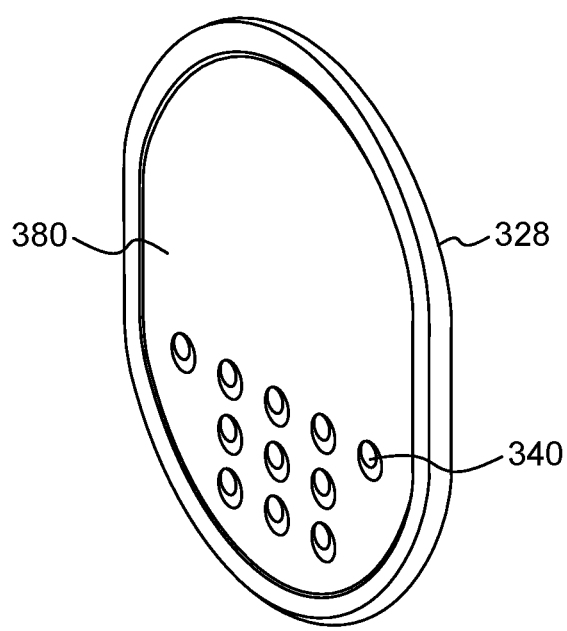
FIG. 20 is a perspective view of a screen for an air bubble suspension apparatus according to an embodiment of the present disclosure.
Figure 21:
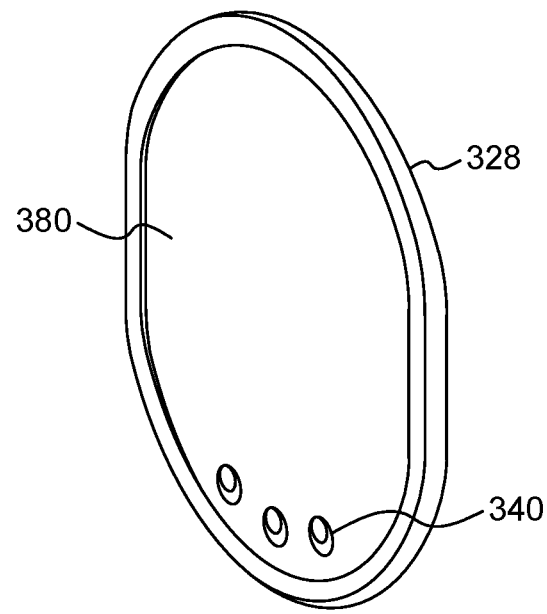
FIG. 21 is a perspective view of a screen for an air bubble suspension apparatus according to an embodiment of the present disclosure.

Referring now to FIGS. 19-24 various embodiments of the screen 328 are shown which are suitable for use in embodiments of the air bubble suspension apparatuses 300 described herein in connection with FIGS. 9-13 and 17-18. Referring to FIG. 19, screen 328 may include a plurality of apertures 340 distributed substantially uniformly over screen 328.

Referring next to FIGS. 20-24, the screen 328 may include a solid portion 380 impermeable to fluid and air, and one or more apertures 340 located outside of the solid portion 380, for example located on portion of screen 328 proximal to the distal outlet of extension tube 370 when assembled. The screen 328 may be positioned in the air bubble suspension apparatus 300 such that the solid portion 380 is adjacent the extension tube 370. Injection fluid entering the internal chamber 320 via the extension tube 370 must therefore enter the vortex flow path B and circulate within the internal chamber 320 at least once prior to reaching the one or more apertures 340. In the embodiment shown in FIG. 20, the solid portion 380 occupies approximately one half of the screen 328 and the one or more apertures 340 occupy approximately one half of the screen 328. In the embodiment shown in FIG. 21, the solid portion 380 occupies a larger proportion of the screen 328 than the one or more apertures 340. In some embodiments, the one or more apertures 340 may be arranged in any pattern such as a grid, arc, or line. In some embodiments, the one or more apertures 340 may be non-uniformly distributed over the screen 328.

Figure 22:
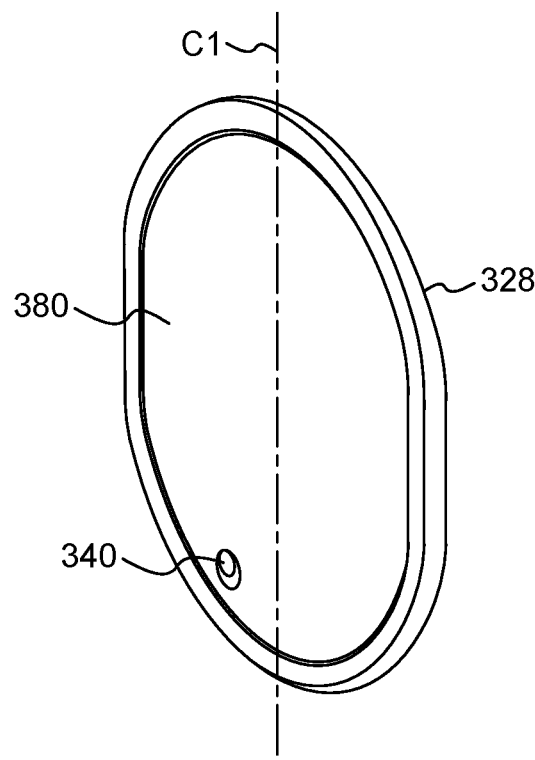
FIG. 22 is a perspective view of a screen for an air bubble suspension apparatus according to an embodiment of the present disclosure.

In the embodiment shown in FIG. 22, the screen 328 includes a single aperture 340 offset from a centerline CL of the screen 328. The solid portion 380 occupies the remainder of the screen 328. Offsetting the aperture 340 from the centerline CL of the screen 328 may force air bubbles in the internal chamber 320 (see FIGS. 17-18) to change direction in order to reach and pass through the aperture 340, thereby further delaying the flow of air bubbles out of the air bubble suspension apparatuses 300.

Figure 23:
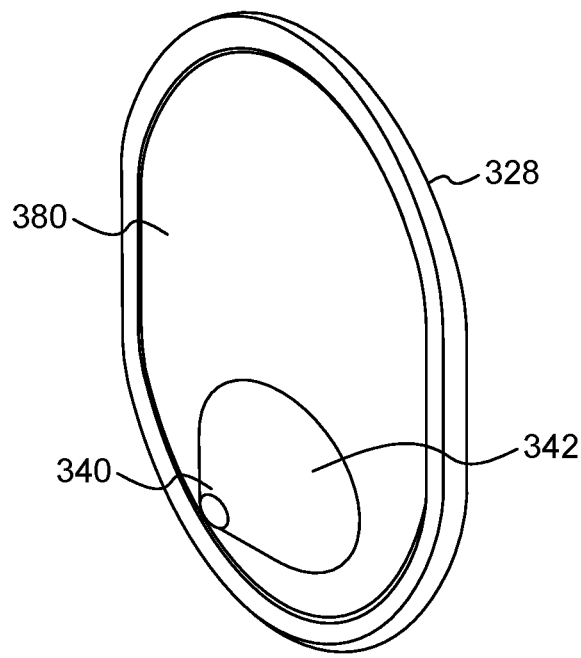
FIG. 23 is a perspective view of a screen for an air bubble suspension apparatus according to an embodiment of the present disclosure.

Referring next to FIG. 23, the screen 328 may include at least one funnel 342 defining the at least one aperture 340. The funnel 342 may taper from a maximum cross-sectional area adjacent the inlet portion 332 of the internal chamber 320 to a minimum diameter extending into the outlet portion 334 of the internal chamber 320 (see FIGS. 9-14 and 17-18).

Figure 24:
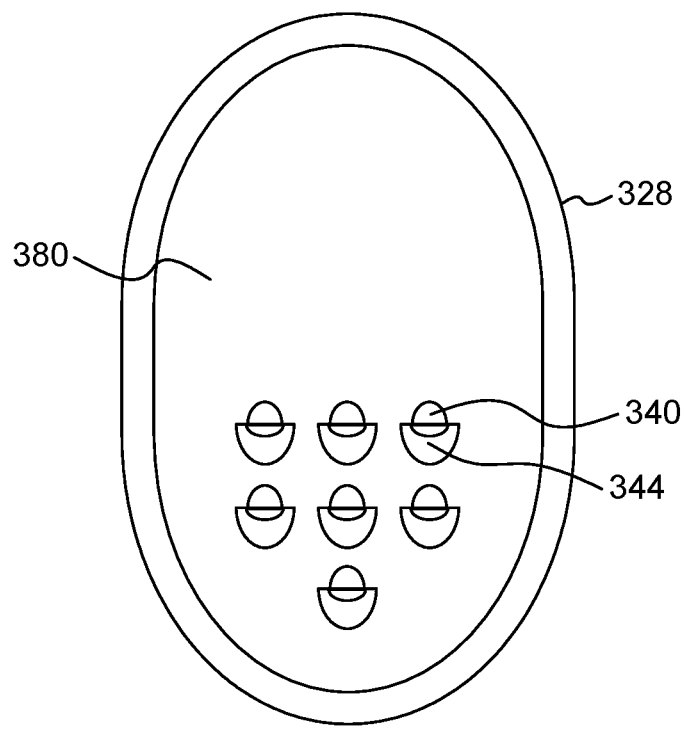
FIG. 24 is a front view of a screen for an air bubble suspension apparatus according to an embodiment of the present disclosure.

Referring next to FIG. 24, in some embodiments of screen 328 each of the one or more apertures 340 may be partially obstructed by a hood 344. Each hood 344 may extend from the screen 328 into the inlet portion 332 of the internal chamber 320 (see FIGS. 17-18), and against the fluid flow direction such that fluid and any associated air bubbles in the inlet portion 332 must flow around the hood 344 to pass through the associated aperture 340. In some embodiments, the hoods 344 may be configured such that air bubbles adhere to the hoods 344, for example via surface tension, to delay flow of air bubbles out of the inlet portion 332.

In all of the embodiments of the screen 328 shown in FIGS. 19-24, the screen 328 may have a hydrophilic coating that induces air bubbles in the injection fluid to adhere to the screen 328, and thereby at least temporarily delaying the flow of such air bubbles toward the outlet fluid pathway 314. In various embodiments, other surfaces of the internal chamber 320 may be at least partially coated with a hydrophilic coating. Further, any portion of the screen 328 or the various features thereof may be configured such that air bubbles adhere to the screen 328, for example via surface tension, to delay flow of the air bubbles through the one or more apertures 340. In some embodiments, the screen 328 may be a mesh, for example made from a material that readily adheres air bubbles to the surface thereof.

According to certain embodiments, the change in fluid pressure across the screen 328 may be substantially zero, so that there is no significant change in fluid velocity at the screen 328 that may dislodge any air bubbles adhered to the screen 328. Instead, the injection fluid may freely flow through other apertures 340 or pathways in the screen instead of dislodging any air bubbles adhered to the screen 328. For example, the volume of inlet portion 332 (see FIGS. 17-18) upstream of the screen 328 may be substantially the same as the volume of outlet portion 334 (see FIGS. 17-18) immediately downstream of the screen 328 so that there is no significant change in fluid pressure due to flow path restriction.

It should be understood that features of the various embodiments of the screen 328 shown in the embodiments of FIGS. 19-24 may be combined with one another and still fall within the scope of the present disclosure.

Figure 25:
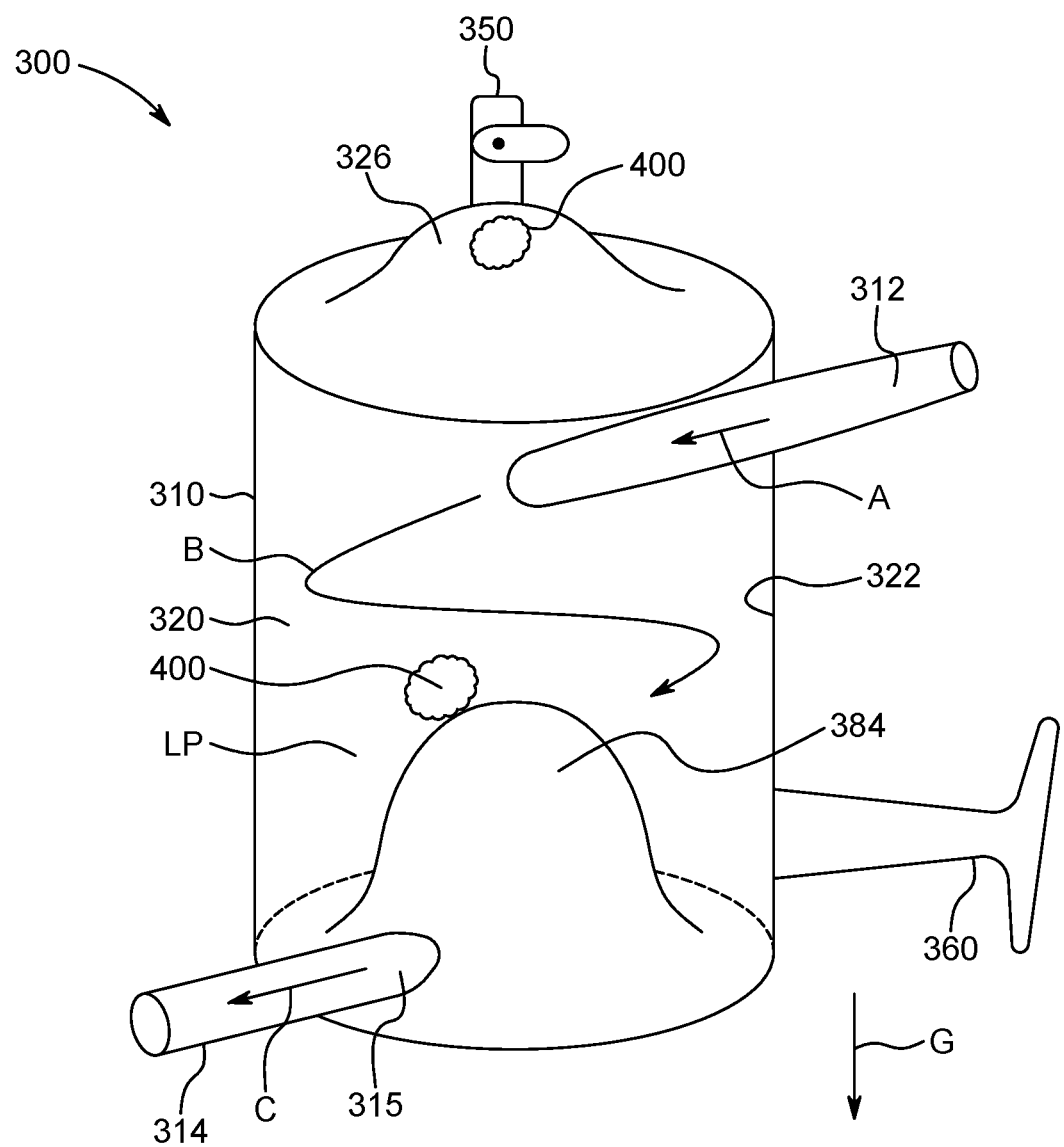
FIG. 25 is a perspective view of an air bubble suspension apparatus according to an embodiment of the present disclosure.

Referring now to FIG. 25, various embodiments of the air bubble suspension apparatus 300 may include a generally cylindrical housing 310 from which the inlet fluid pathway 312 and the outlet fluid pathway 314 extend. The inlet fluid pathway 312 and the outlet fluid pathway 314 may be in fluid communication with opposing ends of the internal chamber 320. As injection fluid is introduced into the internal chamber 320 via the inlet fluid pathway 312 in a direction substantially tangential to the arc of the cylindrical housing 310, an internal fluid vortex is generated in the form of a spiral or helical vortex flow path B flowing along the interior wall 322 of the internal chamber 320. One or more air bubbles 400 carried by the injection fluid migrate towards the low pressure region LP at the center of the vortex flow path B. The injection fluid in the vortex flow path B forms a boundary at least temporarily preventing the one or more air bubbles 400 from flowing to the outlet fluid pathway 314. The length of the spiral or helical vortex flow path B may be proportional to the height of the housing 310. Therefore, the height of the housing 310 may be proportional to the time for which flow of the air bubbles 400 is delayed within the internal chamber 320. Thus, increasing the cylindrical height of housing 310 may result in an increased suspension time of the one or more air bubbles 400 in the helical vortex flow path B.

With continued reference to FIG. 25, the air bubble suspension apparatus 300 may be rotated from the injection position to the priming position by the controller 900 (see FIG. 2) or manually by a user. In the injection position shown in FIG. 25, the air bubble suspension apparatus 300 may be oriented such that the outlet fluid pathway 314 is positioned below the inlet fluid pathway 312. As such, buoyancy of one or more air bubbles 400 within the internal chamber 320 causes the one or more air bubbles 400 to float upward in the internal chamber 320, against the direction of gravity G and the direction of vortex flow path B and away from the outlet fluid path 314.

In the priming position, the air bubble suspension apparatus 300 may be oriented such that the outlet fluid pathway 314 is positioned above the inlet fluid pathway 312 for example by rotation of the air bubble suspension apparatus 300 by approximately 180° around a lateral axis. As such, buoyancy of one or more air bubbles 400 within the internal chamber 320 causes the one or more air bubbles 400 to float upward in the internal chamber 120 toward the outlet fluid path 314, thereby purging the internal chamber 320 of air under flow of the priming fluid.

The air bubble suspension apparatus 300 may include a connector arm 360 extending from the housing 300. The connector arm 360 may be configured for connection to the injector housing 12 or other feature associated with the flow path or injector system 2000 (see FIGS. 1-2). In particular, the connector arm 360 may be configured to interface with an actuator in communication with the controller 900 (see FIG. 2) of the fluid injector system 2000. The controller 900 may be programmed or configured to rotate the air bubble suspension apparatus 300 between the injection position and the priming position via the connector arm 360 according to an injection protocol. Alternatively, the connector arm 360 may be configured to attach to the fluid injector system in either the injection or priming position and may be configured for a user to manually rotate the air bubble suspension apparatus 300 between the injection position and the priming position via the connector arm 360, for example in response to a prompt by the system on a GUI 11, to prepare the fluid injector for an injection procedure.

In some embodiments, the distal surface of housing 300 may include a protrusion 384 extending upward into the internal chamber 320. The protrusion 384 may be approximately domed, conical, and/or a Gaussian surface. The protrusion 384 may extend any height within the internal chamber 320. In some embodiments, the protrusion 384 may extend up to half of a height of the internal chamber 320. The protrusion 384 may be configured to obstruct the flow of the one or more air bubbles 400 toward the opening 315 of the outlet fluid pathway 314 by extending into the low pressure region LP of the fluid vortex and preventing one or more air bubbles 400 in the low pressure region LP from moving downward past the protrusion 384 towards the outlet fluid pathway 314. The protrusion 384 therefore further suspends the one or more air bubbles 400 in the internal chamber 320 in tandem with the bubble suspension provided by the fluid vortex.

In some embodiments, the housing 300 may include a domed or conical recess 326 extending from a proximal surface of the internal chamber 320, similar in function to the recess 326 of FIGS. 7-8. The recess 326 may receive and retain one or more air bubbles 400 floating upward in the internal chamber 320 under the influence of buoyancy to remove the one or more air bubbles 400 from the vortex flow path B. The recess 326 may also be adapted to receive and retain one or more air bubbles in the form of microbubbles generated by outgassing of a medical fluid. In some embodiments, an air purge valve 350 as described in connection with FIG. 6 may be disposed on the housing 300 in fluid communication with the recess 326 such that the one or more air bubbles 400 accumulated in the recess 326 can be removed from the recess 326 as described herein.

In all embodiments of the air bubble suspension apparatus 300 described herein, the housing 310 may be at least partially constructed of a transparent or semi-transparent light-transmissible material, such as polycarbonate, that may act as a light tube. By directing a light source to the housing 310, the one or more bubbles 400, 402, 404, 406, 408 can be illuminated such that the operator can more easily discern the presence of air bubbles in the air bubble suspension apparatus 300.

It should be understood that features of the various embodiments of the air bubble suspension apparatus 300 shown in the embodiments of FIGS. 3-25 may be combined with one another and still fall within the scope of the present disclosure.

While various examples of the present disclosure were provided in the foregoing description, those skilled in the art may make modifications and alterations to these examples without departing from the scope and spirit of the disclosure. For example, it is to be understood that features of various embodiments described herein may be adapted to other embodiments described herein. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. An apparatus for suspending air bubbles in a fluid path of a fluid injector system, the apparatus comprising:
  a housing;
  an internal chamber having a curved, hemispherical interior wall defined within the housing, wherein the internal chamber is at least partly spherical or hemispherical;
  an inlet fluid pathway in fluid communication with the internal chamber, the inlet fluid pathway extending into the internal chamber at a tangent to the curved, hemispherical interior wall; and
  an outlet fluid pathway in fluid communication with the internal chamber, the outlet fluid pathway spaced from the inlet fluid pathway such that an injection fluid flowing into the internal chamber via the inlet fluid pathway is directed away from the outlet fluid pathway,
  wherein the internal chamber is configured to create an internal fluid vortex in the injection fluid entering the internal chamber from the inlet fluid pathway, and wherein the internal fluid vortex defines a circular fluid vortex flow path (B) along the curved, hemispherical interior wall, wherein the circular fluid vortex flow path (B) flows transversely across an opening of the outlet fluid pathway, and wherein the internal fluid vortex at least temporarily suspends the one or more air bubbles in a low pressure region in the center of the circular fluid vortex flow path (B) and delays passage of the one or more air bubbles to the outlet fluid pathway.

2. The apparatus according to claim 1, wherein the outlet fluid pathway extends from the internal chamber in a direction perpendicular to the circular fluid vortex flow path (B) of fluid within the internal chamber.

3. The apparatus according to claim 1, wherein at least a portion of the outlet fluid pathway has a cross-sectional area greater than a cross-sectional area of the inlet fluid pathway to reduce fluid velocity in the outlet fluid pathway relative to fluid velocity in the inlet fluid pathway.

4. The apparatus according to claim 1, wherein the outlet fluid pathway extends substantially parallel to the inlet fluid pathway.

5. The apparatus according to claim 1, wherein the housing comprises:
  a first housing section comprising the inlet fluid pathway and the outlet fluid pathway; and
  a second housing section comprising at least a portion of the internal chamber,
  wherein one of the first housing section and the second housing section comprises a flange for receiving an end feature of the other of the first housing section and the second housing section.

6. The apparatus according to claim 5, wherein the housing comprises at least one strengthening rib extending radially outward from at least a portion of the inlet fluid pathway, the outlet fluid pathway, the second housing section, or the first housing section.

7. The apparatus according to claim 1, further comprising a screen disposed in the outlet fluid pathway such that fluid flowing out of the internal chamber passes through the screen.

8. The apparatus according to claim 1, wherein the housing comprises a light-transmissible material configured to illuminate the air bubbles in the internal chamber.

9. The apparatus according to claim 1, further comprising:
an extension tube in fluid communication with the inlet fluid pathway and extending into the internal chamber, the extension tube comprising a tip spaced apart from the outlet fluid pathway such that fluid flowing into the internal chamber via the extension tube is directed away from the outlet fluid pathway.

10. The apparatus according to claim 9, further comprising a screen dividing the internal chamber into an inlet portion and an outlet portion,
wherein the screen comprises at least one aperture providing fluid communication between the inlet portion and the outlet portion, and
wherein fluid flowing into the internal chamber from the extension tube must flow through the at least one aperture of the screen to reach the outlet fluid pathway.

11. The apparatus according to claim 10, wherein a first portion of the screen adjacent to the tip of the extension tube is impermeable to fluid, and wherein a second portion of the screen adjacent to the outlet fluid pathway comprises the at least one aperture.

12. The apparatus according to claim 9, wherein the housing comprises:
a first housing section comprising a flange configured to receive a screen; and
a second housing section having an end feature received within the flange of the first housing section to capture the screen between the first housing section and the second housing section.

13. The apparatus according to claim 9, wherein the inlet fluid pathway tapers from a smaller cross-sectional area to a larger cross-sectional area in a direction of fluid flow through the inlet fluid pathway to reduce flow velocity of fluid flowing through the inlet fluid pathway.

14. The apparatus according to claim 9, wherein the extension tube extends parallel to an inner wall of the internal chamber.

15. The apparatus according to claim 9, wherein the housing comprises a light-transmissible material configured to illuminate the air bubbles in the internal chamber.

16. A fluid injector system comprising:
at least one fluid reservoir configured for injecting medical fluid;
at least one bubble suspension apparatus in fluid communication with the at least one fluid reservoir; the at least one bubble suspension apparatus comprising:
a housing defining an internal chamber, wherein the internal chamber has a curved, hemispherical interior wall and wherein the internal chamber is at least partly spherical or hemispherical;
an inlet fluid pathway in fluid communication with the internal chamber, wherein the inlet fluid pathway extends into the internal chamber at a tangent to the curved, hemispherical wall;
an outlet fluid pathway in fluid communication with the internal chamber, the outlet fluid pathway spaced from the inlet fluid pathway such that an injection fluid flowing into the internal chamber via the inlet fluid pathway is directed away from the outlet fluid pathway;
at least one upstream air detector configured to detect one or more air bubbles in an air detection tubing region connecting the at least one fluid reservoir to the at least one bubble suspension apparatus; and
at least one shutoff valve downstream of the at least one bubble suspension apparatus and configured to move from an open position to a closed position in response to the at least one upstream air detector detecting the one or more air bubbles in the air detection tubing region,
wherein the internal chamber is configured to create an internal fluid vortex in the injection fluid entering the internal chamber from the inlet fluid pathway, and wherein the internal fluid vortex defines a circular fluid vortex flow path (B) along the curved, hemispherical interior wall, wherein the circular fluid vortex flow path (B) flows transversely across an opening of the outlet fluid pathway, and wherein the internal fluid vortex at least temporarily suspends the one or more air bubbles in a low pressure region in the injection fluid in the center of the circular fluid vortex flow path (B) and delays the passage of the one or more air bubbles to the outlet fluid pathway.

17. The fluid injector system according to claim 16, wherein the at least one bubble suspension apparatus is movable between:
an injection position in which the outlet fluid pathway extends substantially vertically downward from the internal chamber such that a buoyancy of the one or more air bubbles in the internal chamber further induces the one or more air bubbles to remain suspended in the internal fluid vortex in the internal chamber; and
a priming position in which the outlet fluid pathway extends substantially vertically upward from the internal chamber such that the buoyancy of the one or more air bubbles in the internal chamber induces the one or more air bubbles to flow from the internal fluid vortex through the outlet fluid pathway.

18. The fluid injector system according to claim 16, wherein the inlet fluid pathway extends into the internal chamber at a tangent to the at least one curved, hemispherical interior wall.

19. The fluid injector system according to claim 16, wherein the outlet fluid pathway extends from the internal chamber in a direction substantially perpendicular to the circular fluid vortex flow path (B) of fluid in the internal fluid vortex within the internal chamber.

20. The fluid injector system according to claim 16, wherein the outlet fluid pathway extends substantially parallel to the inlet fluid pathway.

21. The fluid injector system according to claim 16, wherein the internal chamber is at least partially spherical or hemispherical.

* * * * *

UNITED STATES PATENT AND TRADEMARK OFFICE
CERTIFICATE OF CORRECTION

| | | |
|---|---|---|
| PATENT NO. | : 11,839,751 B2 | |
| APPLICATION NO. | : 17/999092 | |
| DATED | : December 12, 2023 | |
| INVENTOR(S) | : Cowan et al. | |

It is certified that error appears in the above-identified patent and that said Letters Patent is hereby corrected as shown below:

In the Specification

In Column 16, Line 6, delete "210B" and insert -- 210B. --, therefor.
In Column 21, Line 22, delete "some embodiments" and insert -- in some embodiments, --, therefor.
In Column 26, Line 61, delete "FIGS. 19-24" and insert -- FIGS. 19-24, --, therefor.

In the Claims

In Column 32, Line 24, in Claim 16, delete "the passage" and insert -- passage --, therefor.

Signed and Sealed this
Eighth Day of October, 2024

Katherine Kelly Vidal
*Director of the United States Patent and Trademark Office*